United States Patent
Wang et al.

(10) Patent No.: US 10,214,534 B2
(45) Date of Patent: Feb. 26, 2019

(54) SUBSTITUTED 2-PHENYL (AZA)BENZOFURAN COMPOUNDS FOR THE TREATMENT OF HEPATITIS C

(71) Applicant: BRISTOL-MYERS SQUIBB COMPANY, Princeton, NJ (US)

(72) Inventors: Tao Wang, Farmington, CT (US); Zhongxing Zhang, Madison, CT (US); Kyle E. Parcella, Wallingford, CT (US); Kyle J. Eastman, Wallingford, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/317,541

(22) PCT Filed: Jun. 10, 2015

(86) PCT No.: PCT/US2015/034999
§ 371 (c)(1),
(2) Date: Dec. 9, 2016

(87) PCT Pub. No.: WO2015/191653
PCT Pub. Date: Dec. 17, 2015

(65) Prior Publication Data
US 2017/0121340 A1    May 4, 2017

Related U.S. Application Data

(60) Provisional application No. 62/010,717, filed on Jun. 11, 2014.

(51) Int. Cl.
| | | |
|---|---|---|
| *C07D 491/048* | (2006.01) | |
| *C07D 405/12* | (2006.01) | |
| *C07D 491/04* | (2006.01) | |
| *C07D 307/84* | (2006.01) | |

(52) U.S. Cl.
CPC ........ *C07D 491/048* (2013.01); *C07D 307/84* (2013.01); *C07D 405/12* (2013.01); *C07D 491/04* (2013.01)

(58) Field of Classification Search
CPC .................................................. C07D 491/048
See application file for complete search history.

(56) References Cited

U.S. PATENT DOCUMENTS

| 8,445,497 B2 | 5/2013 | Yeung et al. |
| 9,096,580 B2 | 8/2015 | Yeung |
| 2016/0024103 A1 | 1/2016 | Yeung et al. |

FOREIGN PATENT DOCUMENTS

WO    WO 2012003164 A1 *   1/2012   ........... A61K 31/343

* cited by examiner

*Primary Examiner* — Andrew D Kosar
*Assistant Examiner* — John S Kenyon
(74) *Attorney, Agent, or Firm* — John F. Levis

(57) ABSTRACT

Compounds of Formula I, including their salts, as well as compositions and methods of using the compounds are set forth. The compounds have activity against hepatitis C virus (HCV) and may be useful in treating those infected with HCV:

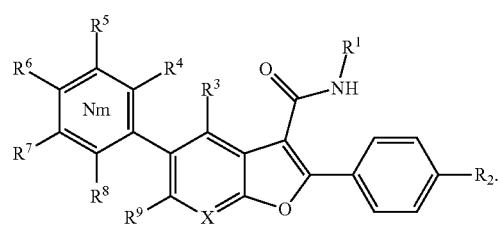

I

8 Claims, No Drawings

SUBSTITUTED 2-PHENYL (AZA)BENZOFURAN COMPOUNDS FOR THE TREATMENT OF HEPATITIS C

CROSS REFERENCE TO RELATED APPLICATION

This non-provisional application claims the benefit of U.S. Provisional Application Ser. No. 62/010,717 filed Jun. 11, 2014 which is herein incorporated by reference in its entirety.

FIELD OF THE INVENTION

The invention relates to novel compounds, including their salts, which have activity against hepatitis C virus (HCV) and which are useful in treating those infected with HCV. The invention also relates to compositions and methods of making and using these compounds.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, has shown an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201 describe compounds of the HCV-796 class. Other compounds have been disclosed; see for example, WO2009/101022, as well as WO 2012/058125.

What is therefore needed in the art are additional compounds which are novel and effective against hepatitis C. Additionally, these compounds should provide advantages for pharmaceutical uses, for example, with regard to one or more of their mechanism of action, binding, inhibition efficacy, target selectivity, solubility, safety profiles, or bioavailability. Also needed are new formulations and methods of treatment which utilize these compounds.

SUMMARY OF THE INVENTION

One aspect of the invention is a compound of Formula I, including pharmaceutically acceptable salts thereof:

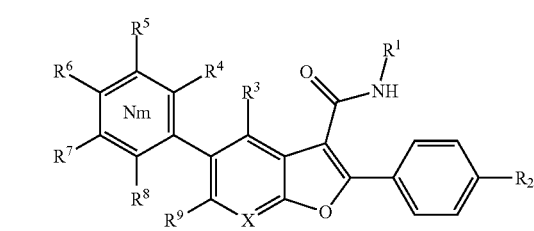

wherein
m is 0 or 1;
X is N or C—$R^{10}$;
$R^1$ is methyl;
$R^2$ is selected from the group of $R^{101}$, $OR^{101}$, $NR^{102}R^{103}$, $SR^{101}$, $OAr^1$, $NR^{102}Ar^1$, and $SAr^1$;

$R^{101}$ is hydrogen, alkyl or cycloalkyl with 0-3 substituents selected from the group of halo, CN, amide, ester, hydroxyl, alkoxy, and haloalkoxy;

$R^{102}$, $R^{103}$ are each independently hydrogen, alkyl or cycloalkyl with 0-3 substituents selected from the group of halo, hydroxyl, alkoxy, and haloalkoxy; or $R^{102}$ and $R^{103}$ can form a ring by joining two atoms, one from each of $R^{102}$ and $R^{103}$;

$Ar^1$ is phenyl, 5-membered heteroaryl or 6-membered heteroaryl, and is substituted with 0-3 substituents selected from the group of cyano, halo, alkyl, cycloalkyl, haloalkyl, OH, $OR^{104}$, haloalkoxy, $NH_2$, $NR^{105}R^{106}$, $COOR^{104}$, $CONR^{105}R^{106}$, $S(O)_2R^{104}$, $S(O)_2NR^{105}R^{106}$, and $NR^{104}CONR^{105}R^{106}$;

$R^{104}$ is hydrogen, alkyl or cycloalkyl with 0-3 substituents selected from the group of halo, hydroxyl, alkoxy, and haloalkoxy;

$R^{105}$, $R^{106}$ are each independently hydrogen, alkyl or cycloalkyl with 0-3 substituents selected from the group of halo, hydroxyl, alkoxy, and haloalkoxy; or $R^{105}$ and $R^{106}$ can form a ring by joining two atoms, one from each of $R^{105}$ and $R^{106}$;

$R^3$ is hydrogen, halo, or alkyl;

$R^4$, $R^5$, $R^6$, $R^7$, $R^8$ are each independently selected from the group of hydrogen, halo, alkyl, cycloalkyl, haloalkyl, halocycloalkyl, hydroxyalkyl, hydroxycycloalkyl, alkoxyalkyl, alkoxycycloalkyl, alkoxy, hydroxyalkyloxy, alkoxyalkyloxy, $COOR^{201}$ and $CON(R^{202})(R^{203})$;

$R^{201}$ is hydrogen, alkyl or cycloalkyl with 0-3 substituents selected from the group of halo, hydroxyl, alkoxy, and haloalkoxy;

$R^{202}$, $R^{203}$ are each independently selected from the group of hydrogen, alkyl, cycloalkyl, alkenyl, cycloalkyl alkynyl, cyclic ether, cyclic amine, lactame, fused bicyclic alkyl, bridged bicyclic alkyl, spiro bicyclic alkyl, fused bicyclic ether, bridged bicyclic ether, spiro bicyclic ether, fused bicyclic amine, bridged bicyclic amine and spiro bicyclic amine, with 0-3 substituents selected from the group of halo, OH, $OR^{104}$, $NH_2$, $NR^{105}R^{106}$, $COOR^{104}$, $CONR^{105}R^{106}$, $S(O)_2R^{104}$, $S(O)_2NR^{105}R^{106}$, $NR^{104}CONR^{105}R^{106}$, $OR^{104}CONR^{105}R^{106}$, $C(=NR^{107})NR^{105}R^{106}$, $NR^{108}C(=NR^{107})NR^{105}R^{106}$, haloalkoxy, $Ar^2$, $O-Ar^2$, and $NR^{105}-Ar^2$; or $R^{202}$ and $R^{203}$ can form a ring by joining two atoms, one from each of $R^{202}$ and $R^{203}$; or $R^{202}$ and $R^{203}$ can form bicyclic or tricyclic rings by joining multiple atoms from of $R^{202}$ and $R^{203}$;

$R^{107}$, $R^{108}$ are each independently hydrogen, alkyl or cycloalkyl with 0-3 substituents selected from the group of halo, hydroxyl, alkoxy, and haloalkoxy; or $R^{107}$ and $R^{108}$ can form a ring by joining two atoms, one from each of $R^{107}$ and $R^{108}$;

$Ar^2$ is phenyl, 5-membered heteroaryl or 6-membered heteroaryl, and is substituted with 0-3 substituents selected from the group of cyano, halo, alkyl, cycloalkyl, haloalkyl, OH, $OR^{204}$, haloalkoxy, $NH_2$, $NR^{205}R^{206}$, $COOR^{204}$, $CONR^{205}R^{206}$, $S(O)_2R^{204}$, $S(O)_2NR^{205}R^{206}$, and $NR^{204}CONR^{205}R^{206}$;

$R^{204}$ is hydrogen, alkyl or cycloalkyl with 0-3 substituents selected from the group of halo, hydroxyl, alkoxy, and haloalkoxy;

$R^{205}$, $R^{206}$ are each independently hydrogen, alkyl or cycloalkyl with 0-3 substituents selected from the group of halo, hydroxyl, alkoxy, and haloalkoxy; or $R^{205}$ and $R^{206}$ can form a ring by joining two atoms, one from each of $R^{205}$ and $R^{206}$;

$R^9$ is selected from the group of hydrogen, halo, alkyl, cycloalkyl, alkoxy, $Ar^3$ and $NR^{301}R^{302}$;

$R^{301}$ is selected from the group of hydrogen, alkyl, cycloalkyl, (cycloalkyl)alkyl, benzyl, alkylcarbonyl, haloalkyl carbonyl, phenyl carbonyl, (alkoxyphenyl)carbonyl, alkylsulfonyl, phenylsulfonyl, (alkoxyphenyl)sulfonyl, and (haloalkoxyphenyl)sulfonyl;

$R^{302}$ is hydrogen, alkyl, hydroxyalkyl, or alkoxyalkyl; or $R^{301}$ and $R^{302}$ taken together with nitrogen to which they are attached is oxazolidinonyl or dioxothiazinyl;

$Ar^3$ is phenyl, 5-membered heteroaryl or 6-membered heteroaryl, and is substituted with 0-3 substituents selected from the group of cyano, halo, alkyl, cycloalkyl, haloalkyl, OH, $OR^{303}$, haloalkoxy, $NH_2$, $NR^{304}R^{305}$, $COOR^{303}$, $CONR^{304}R^{305}$, $S(O)_2R^{303}$, $S(O)_2NR^{304}R^{305}$, and $NR^{303}CONR^{304}R^{305}$;

$R^{303}$ is hydrogen, alkyl or cycloalkyl with 0-3 substituents selected from the group of halo, hydroxyl, alkoxy, and haloalkoxy;

$R^{304}$, $R^{305}$ are each independently hydrogen, alkyl or cycloalkyl with 0-3 substituents selected from the group of halo, hydroxyl, alkoxy, and haloalkoxy; or $R^{304}$ and $R^{305}$ can form a ring by joining two atoms, one from each of $R^{304}$ and $R^{305}$;

$R^{10}$ is selected from the group of hydrogen, alkyl, halo, $N(R^{401})(R^{402})$, and alkylsulfonyl;

$R^{401}$ and $R^{402}$ are each independently selected from the group of hydrogen, alkyl, hydroxyalkyl, alkoxyalkyl, alkylsulfonyl, and alkylsulfonylalkyl;

or $N(R^{401})(R^{402})$ taken together is azetidinyl, pyrrolidinyl, piperidinyl, or piperazinyl, and is substituted with 0-2 substituents selected from alkyl, hydroxyalkyl, and hydroxyl.

The invention also relates to pharmaceutical compositions comprising a compound of Formula I, including a pharmaceutically acceptable salt thereof, and a pharmaceutically acceptable carrier, excipient and/or diluent.

In addition, the invention provides one or more methods of treating hepatitis C infection comprising administering a therapeutically effective amount of a compound of Formula I to a patient.

Also provided as part of the invention are one or more methods for making the compounds of Formula I, as well as any intermediates.

The present invention is directed to these, as well as other important ends, hereinafter described.

DETAILED DESCRIPTION OF THE EMBODIMENTS

As used herein, the singular forms "a", "an", and "the" include plural reference unless the context specifically dictates otherwise.

Unless otherwise specifically set forth elsewhere in the application, the following terms may be used herein and shall have the following meanings: "Hydrogen" or "H" refers to hydrogen, including its isotopes, such as deuterium. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

As set forth above, the invention is directed to one or more compounds of Formula I, including pharmaceutically acceptable salts thereof:

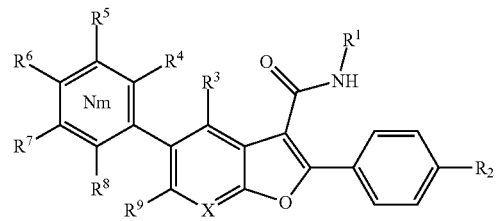

I wherein
m is 0 or 1;
X is N or C—$R^{10}$;
$R^1$ is methyl;
$R^2$ is selected from the group of $R^{101}$, $OR^{101}$, $NR^{102}R^{103}$, $SR^{101}$, $OAr^1$, $NR^{102}Ar^1$ and $SAr^1$;
$R^{101}$ is hydrogen, alkyl or cycloalkyl with 0-3 substituents selected from the group of halo, CN, amide, ester, hydroxyl, alkoxy, and haloalkoxy;
$R^{102}$, $R^{103}$ are each independently hydrogen, alkyl or cycloalkyl with 0-3 substituents selected from the group of halo, hydroxyl, alkoxy, and haloalkoxy; or
$R^{102}$ and $R^{103}$ can form a ring by joining two atoms, one from each of $R^{102}$ and $R^{103}$;
$Ar^1$ is phenyl, 5-membered heteroaryl or 6-membered heteroaryl, and is substituted with 0-3 substituents selected from the group of cyano, halo, alkyl, cycloalkyl, haloalkyl, OH, $OR^{104}$, haloalkoxy, $NH_2$, $NR^{105}R^{106}$, $COOR^{104}$, $CONR^{105}R^{106}$, $S(O)_2R^{104}$, $S(O)_2NR^{105}R^{106}$, and $NR^{104}CONR^{105}R^{106}$;
$R^{104}$ is hydrogen, alkyl or cycloalkyl with 0-3 substituents selected from the group of halo, hydroxyl, alkoxy, and haloalkoxy;
$R^{105}$, $R^{106}$ are each independently hydrogen, alkyl or cycloalkyl with 0-3 substituents selected from the group of halo, hydroxyl, alkoxy, and haloalkoxy; or
$R^{105}$ and $R^{106}$ can form a ring by joining two atoms, one from each of $R^{105}$ and $R^{106}$;
$R^3$ is hydrogen, halo, or alkyl;
$R^4$, $R^5$, $R^6$, $R^7$, $R^8$ are each independently selected from the group of hydrogen, halo, alkyl, cycloalkyl, haloalkyl, halocycloalkyl, hydroxyalkyl, hydroxycycloalkyl, alkoxyalkyl, alkoxycycloalkyl, alkoxy, hydroxyalkyloxy, alkoxyalkyloxy, $COOR^{201}$ and $CON(R^{202})(R^{203})$;
$R^{201}$ is hydrogen, alkyl or cycloalkyl with 0-3 substituents selected from halo, hydroxyl, alkoxy, and haloalkoxy;
$R^{202}$, $R^{203}$ are each independently selected from the group of hydrogen, alkyl, cycloalkyl, alkenyl, cycloalkyl alkynyl, cyclic ether, cyclic amine, lactame, fused bicyclic alkyl, bridged bicyclic alkyl, spiro bicyclic alkyl, fused bicyclic ether, bridged bicyclic ether, spiro bicyclic ether, fused bicyclic amine, bridged bicyclic amine, and spiro bicyclic amine, with 0-3 substituents selected from the group of halo, OH, $OR^{104}$, $NH_2$, $NR^{105}R^{106}$, $COOR^{104}$, $CONR^{105}R^{106}$, $S(O)_2R^{104}$, $S(O)_2NR^{105}R^{106}$, $NR^{104}CONR^{105}R^{106}$, $OR^{104}CONR^{105}R^{106}$, $C(=NR^{107})NR^{105}R^{106}$, $NR^{108}C(=NR^{107})NR^{105}R^{106}$, haloalkoxy, $Ar^2$, $O-Ar^2$, and $NR^{105}-Ar^2$; or
$R^{202}$ and $R^{203}$ can form a ring by joining two atoms, one from each of $R^{202}$ and $R^{203}$;
$R^{202}$ and $R^{203}$ can form bicyclic or tricyclic rings by joining multiple atoms from of $R^{202}$ and $R^{203}$;
$R^{107}$, $R^{108}$ are each independently hydrogen, alkyl or cycloalkyl with 0-3 substituents selected from the group of halo, hydroxyl, alkoxy, and haloalkoxy; or $R^{107}$ and $R^{108}$ can form a ring by joining two atoms, one from each of $R^{107}$ and $R^{108}$;

$Ar^2$ is phenyl, 5-membered heteroaryl or 6-membered heteroaryl, and is substituted with 0-3 substituents selected from the group of cyano, halo, alkyl, cycloalkyl, haloalkyl, OH, $OR^{204}$ haloalkoxy $NH_2$, $NR^{205}R^{206}$, $COOR^{204}$, $CONR^{205}R^{206}$, $S(O)_2R^{204}$, $S(O)_2NR^{205}R^{206}$, and $NR^{204}CONR^{205}R^{206}$;

$R^{204}$ is hydrogen, alkyl or cycloalkyl with 0-3 substituents selected from the group of halo, hydroxyl, alkoxy, and haloalkoxy;

$R^{205}$, $R^{206}$ are each independently hydrogen, alkyl or cycloalkyl with 0-3 substituents selected from the group of halo, hydroxyl, alkoxy, and haloalkoxy; or $R^{205}$ and $R^{206}$ can form a ring by joining two atoms, one from each of $R^{205}$ and $R^{206}$;

$R^9$ is selected from the group of hydrogen, halo, alkyl, cycloalkyl, alkoxy, $Ar^3$ and $NR^{301}R^{302}$;

$R^{301}$ is selected from the group of hydrogen, alkyl, cycloalkyl, (cycloalkyl)alkyl, benzyl, alkylcarbonyl, haloalkyl carbonyl, phenyl carbonyl, (alkoxyphenyl)carbonyl, alkylsulfonyl, phenylsulfonyl, (alkoxyphenyl)sulfonyl, and (haloalkoxyphenyl)sulfonyl;

$R^{302}$ is hydrogen, alkyl, hydroxyalkyl, or alkoxyalkyl; or $R^{301}$ and $R^{302}$ taken together with nitrogen to which they are attached is oxazolidinonyl or dioxothiazinyl;

$Ar^3$ is phenyl, 5-membered heteroaryl or 6-membered heteroaryl, and is substituted with 0-3 substituents selected from the group of cyano, halo, alkyl, cycloalkyl, haloalkyl, OH, $OR^{303}$, haloalkoxy, $NH_2$, $NR^{304}R^{305}$, $COOR^{303}$, $CONR^{304}R^{305}$, $S(O)_2R^{303}$, $S(O)_2NR^{304}R^{305}$, and $NR^{303}CONR^{304}R^{305}$;

$R^{303}$ is hydrogen, alkyl or cycloalkyl with 0-3 substituents selected from halo, hydroxyl, alkoxy, and haloalkoxy;

$R^{304}$, $R^{305}$ are each independently hydrogen, alkyl or cycloalkyl with 0-3 substituents selected from halo, hydroxyl, alkoxy, and haloalkoxy; or $R^{304}$ and $R^{305}$ can form a ring by joining two atoms, one from each of $R^{304}$ and $R^{305}$;

$R^{10}$ is selected from the group of hydrogen, alkyl, halo, $N(R^{401})(R^{402})$, and alkylsulfonyl;

$R^{401}$ and $R^{402}$ are each independently selected from the group of hydrogen, alkyl, hydroxyalkyl, alkoxyalkyl, alkylsulfonyl, and alkylsulfonylalkyl;

or $N(R^{401})(R^{402})$ taken together is azetidinyl, pyrrolidinyl, piperidinyl, or piperazinyl, and is substituted with 0-2 substituents selected from alkyl, hydroxyalkyl, and hydroxy.

In a preferred embodiment of the invention m is 0.

It is also preferred that $R^2$ is $OAr^1$, $OR^{101}$ or $R^{101}$. It is further preferred that $Ar^1$ is phenyl or pyridine. More preferably, the phenyl is substituted with halo, methoxy or alkyl.

Additionally, it is preferred that $R^5$ is $CON(R^{202})(R^{203})$. It is also preferred that $R^{202}$, $R^{203}$ are hydrogen or alkyl.

In certain embodiments it is also preferred that $R^7$ is $CON(R^{202})(R^{203})$. It is also preferred that $R^{202}$, $R^{203}$ are hydrogen or alkyl, which may be further substituted with $COOR^{104}$.

It is also preferred that $R^9$ is $NR^{301}R^{302}$. More preferably, $R^{301}$ is hydrogen, alkyl or alkylsulfonyl. It is further preferred that $R^{302}$ is alkyl.

Also preferred are compounds of Formula I, including pharmaceutically acceptable salts thereof, which are selected from the group of:

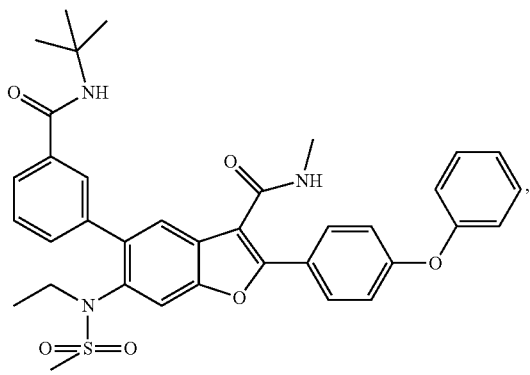

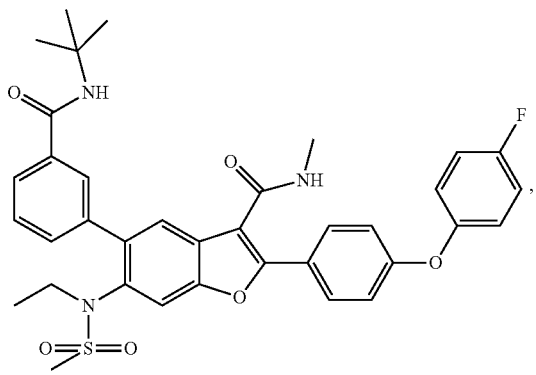

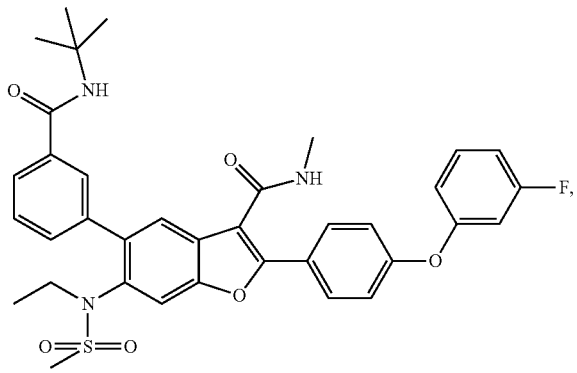

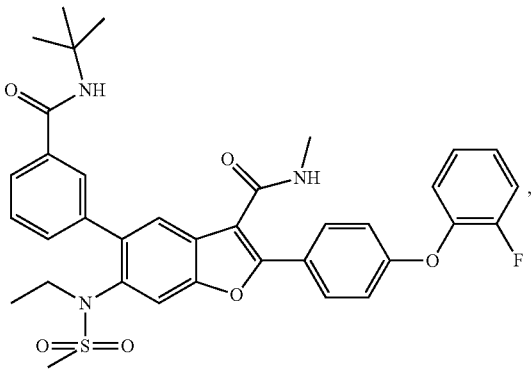

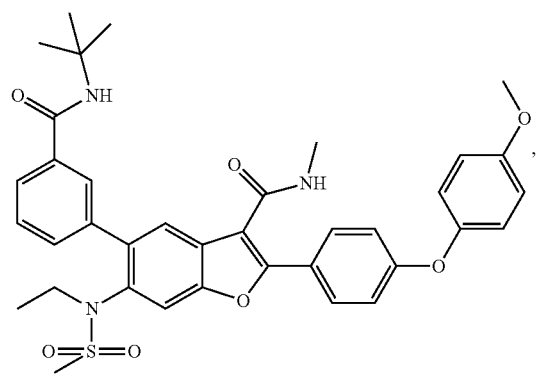
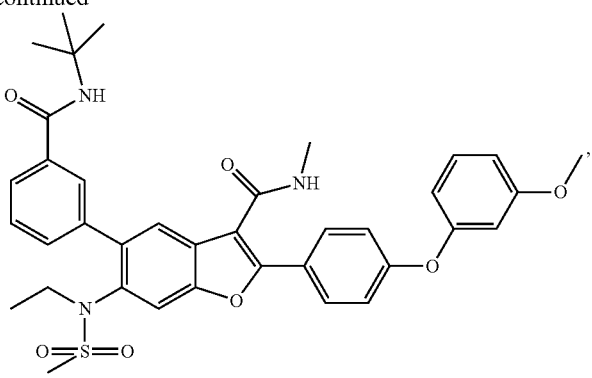
-continued
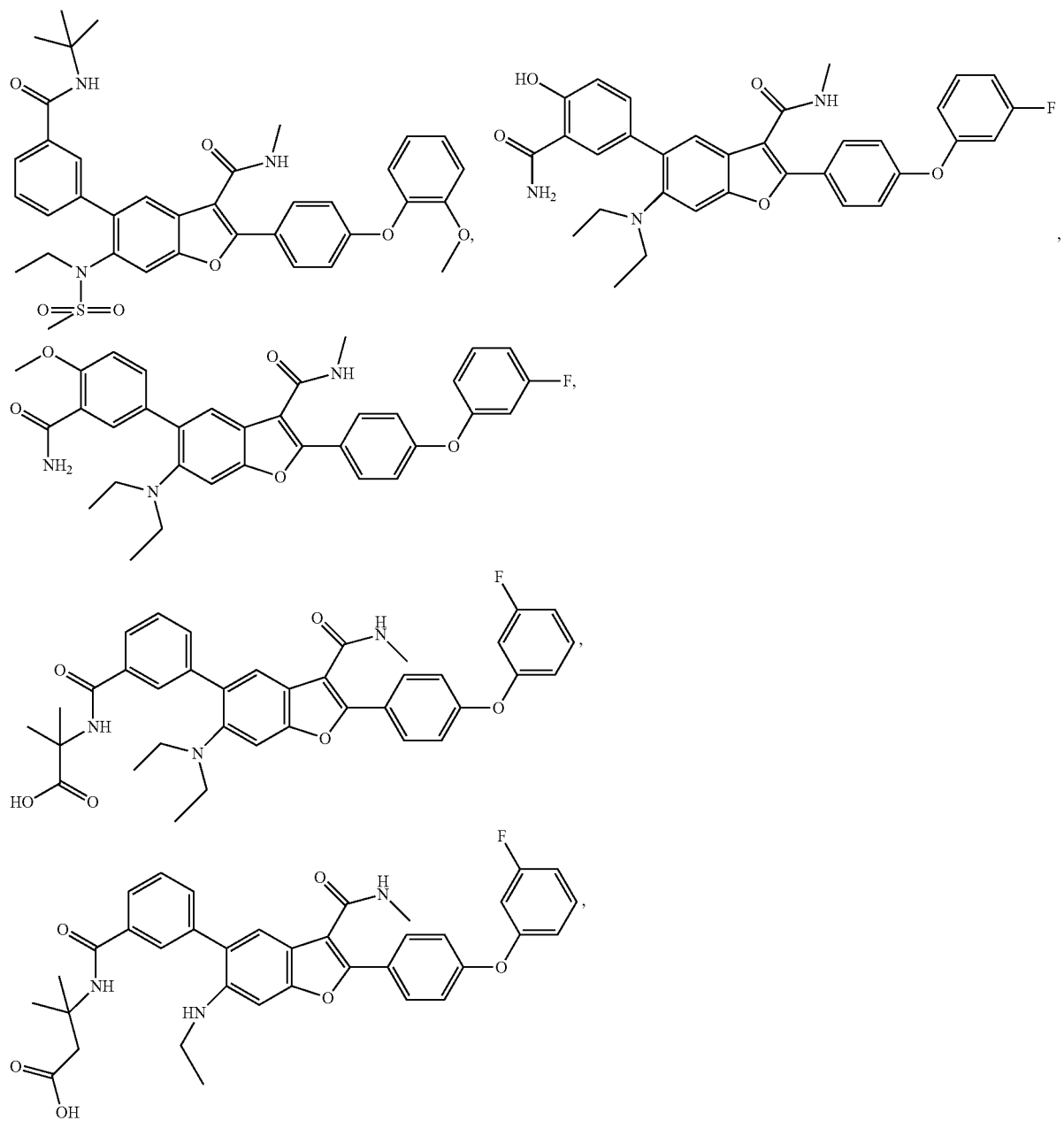

-continued
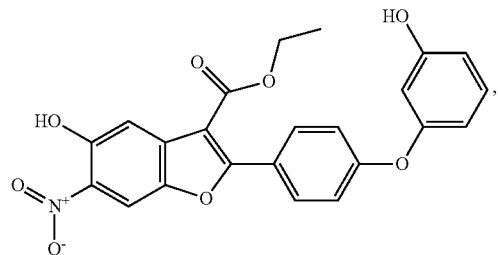
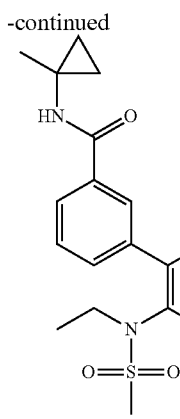
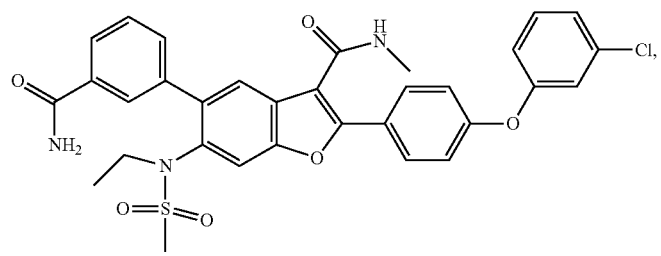
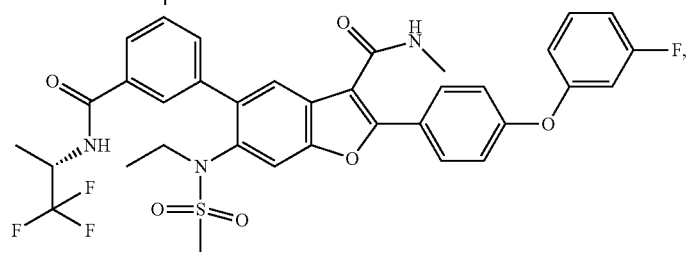
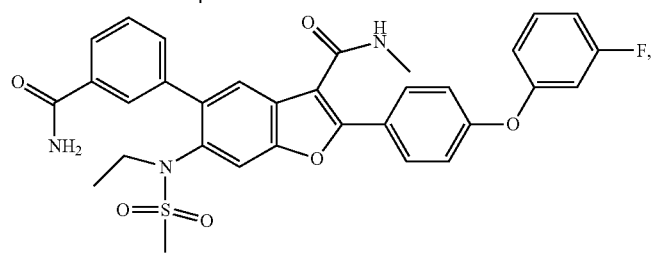
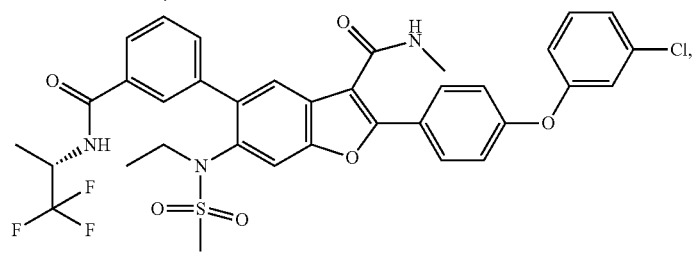
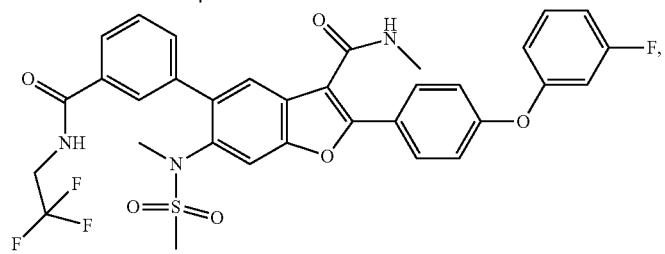

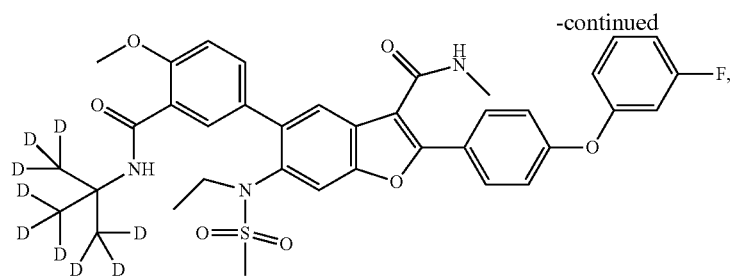
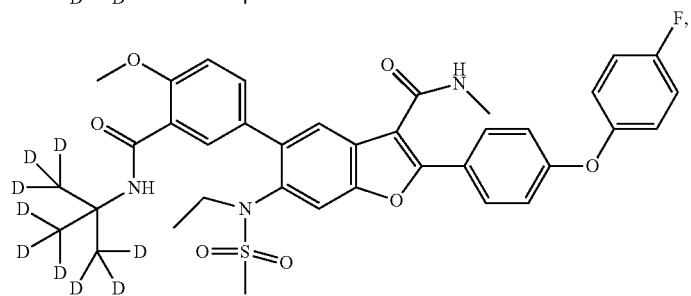
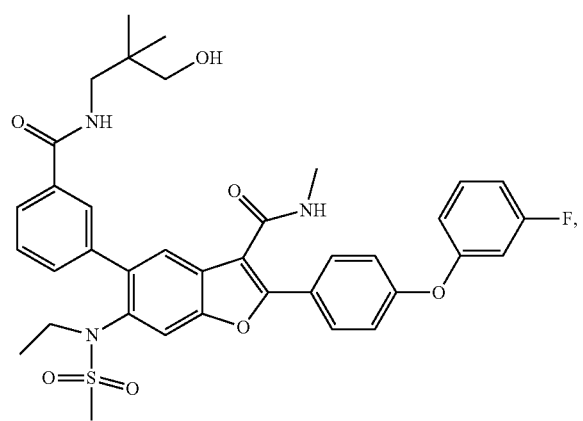
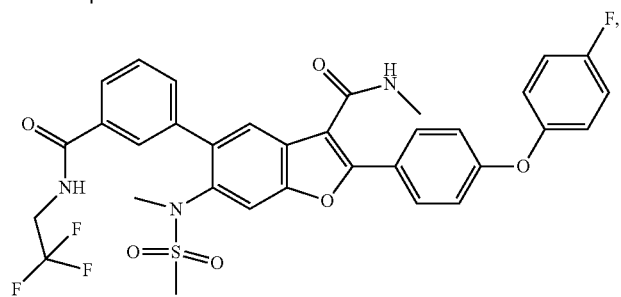
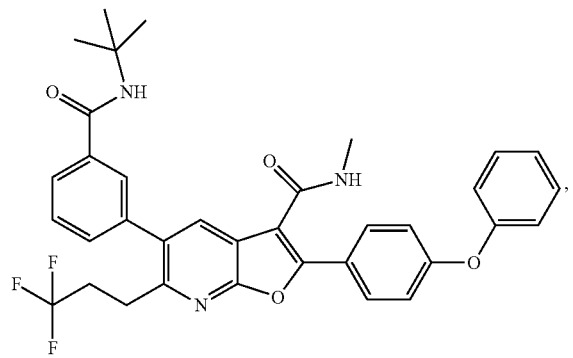
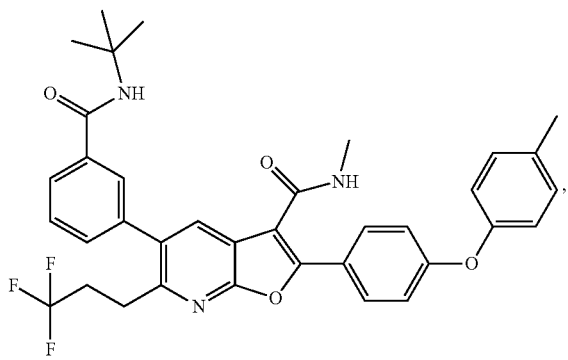

-continued
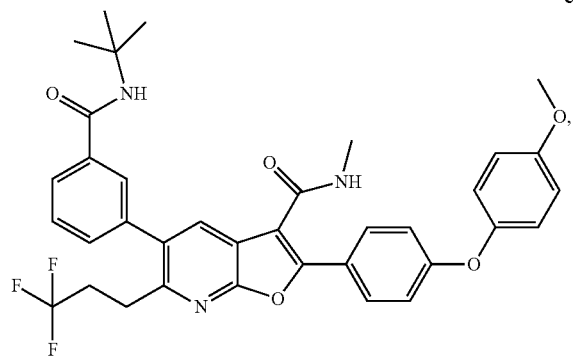
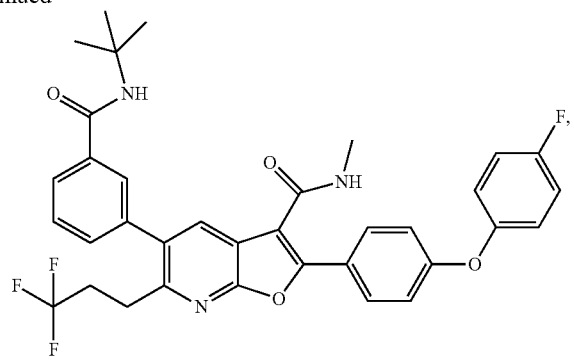
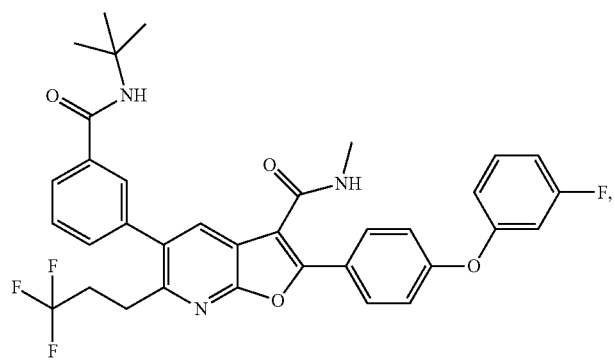
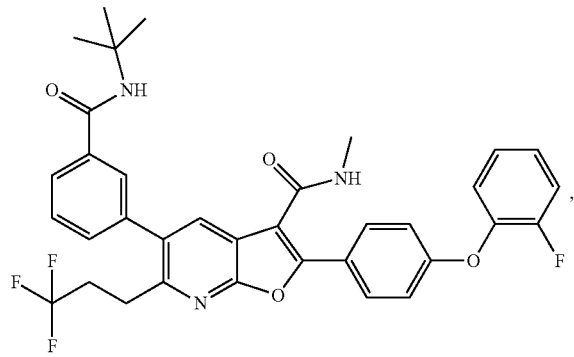
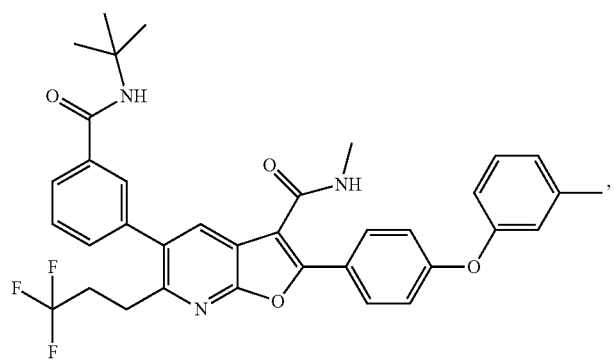
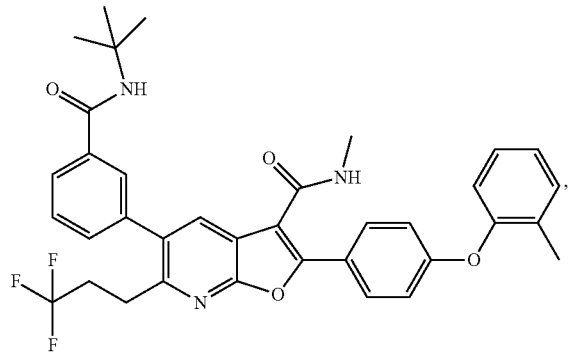
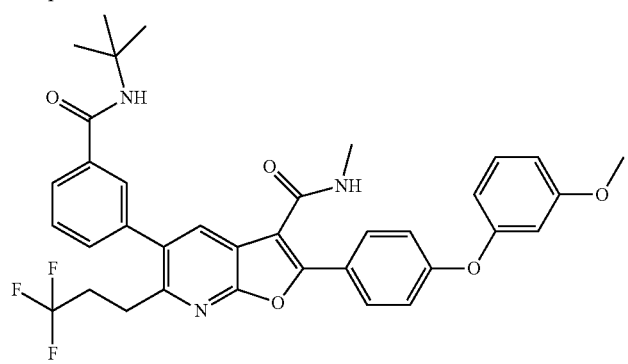
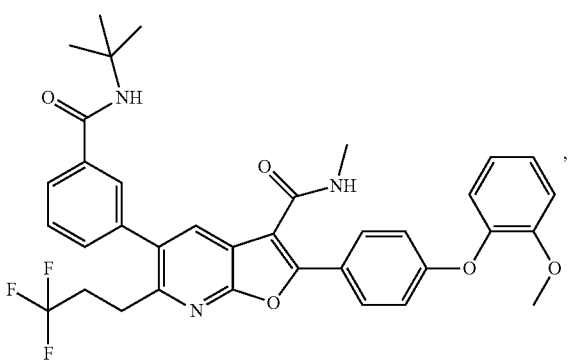

-continued

-continued
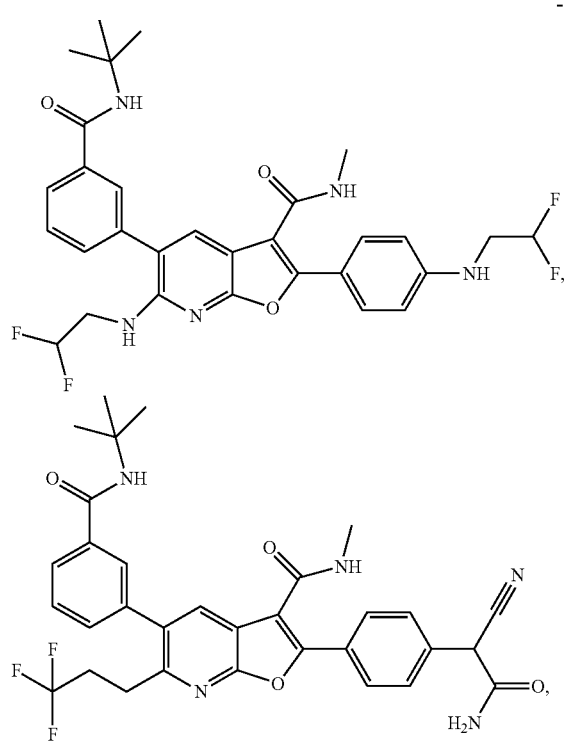
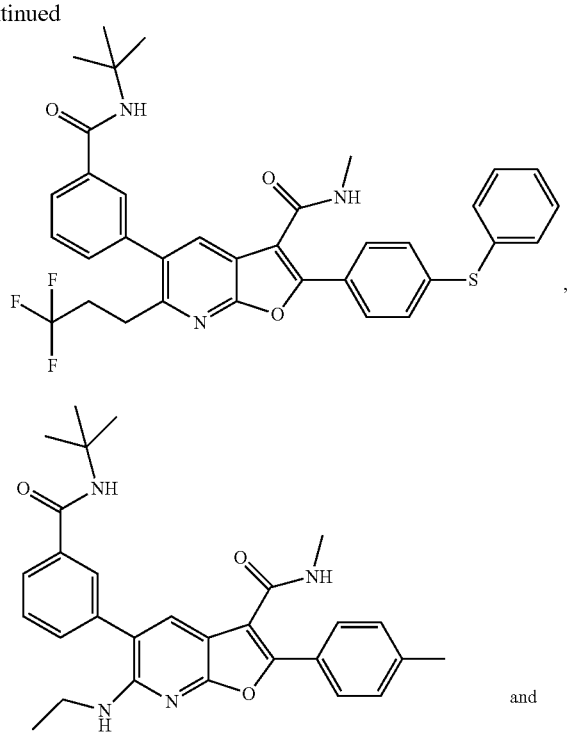
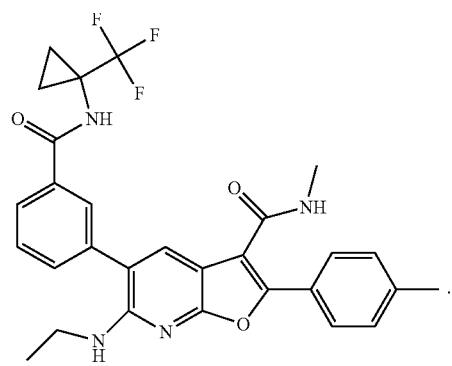
In addition, preferable compounds of Formula I, including pharmaceutically acceptable salts thereof, are selected from the group of:
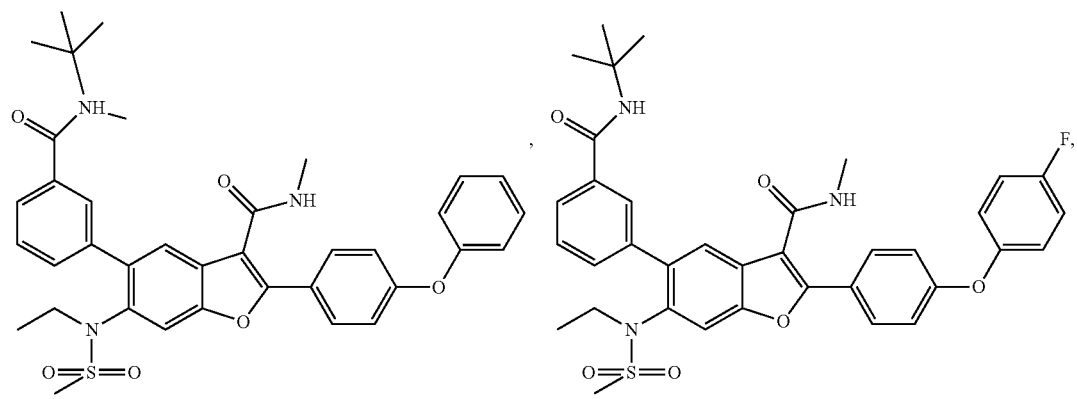

21
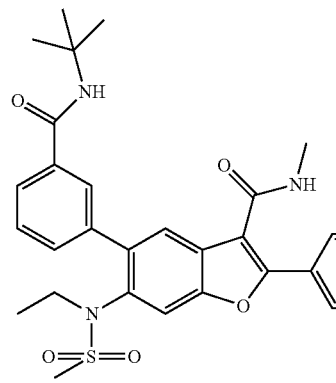
22
-continued
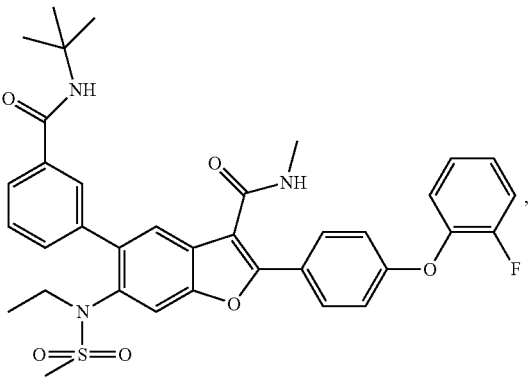
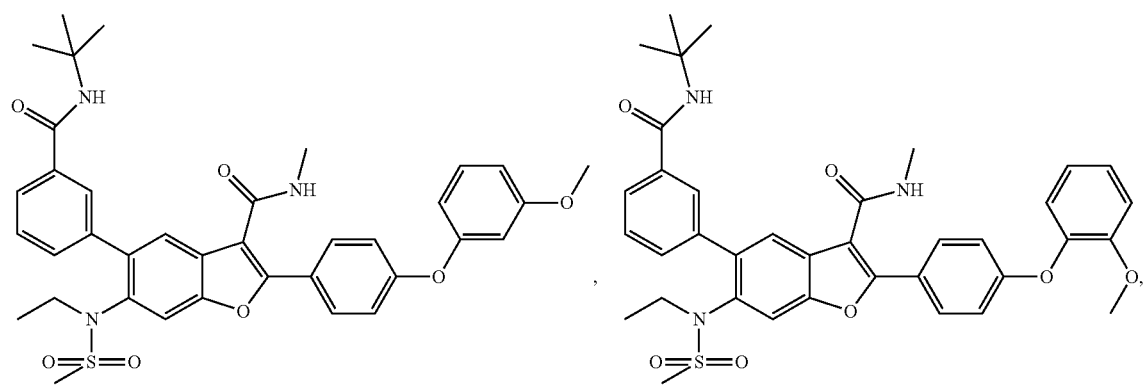
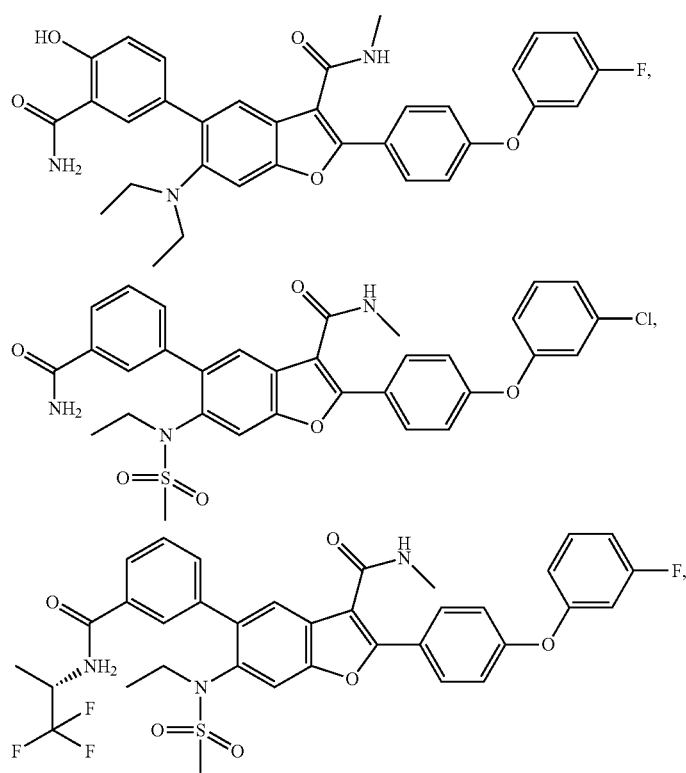

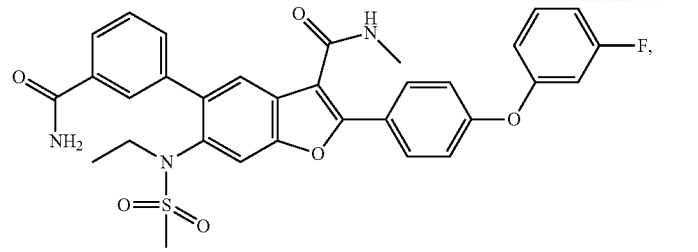
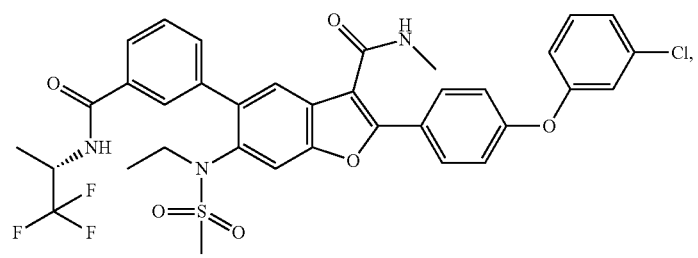
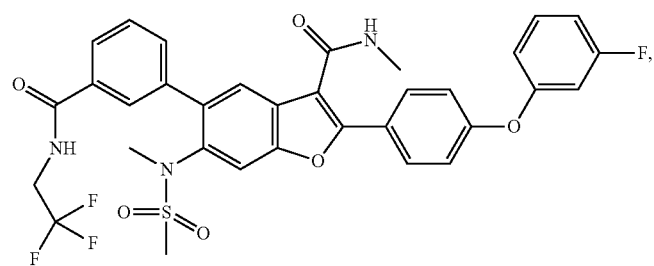
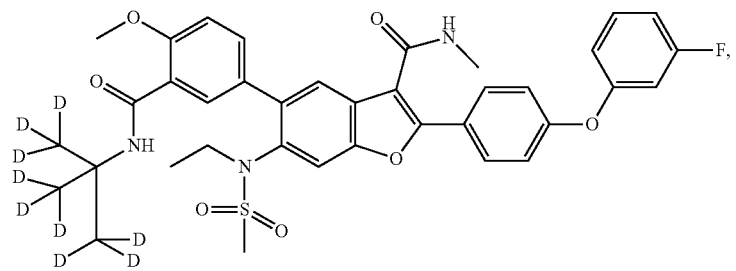
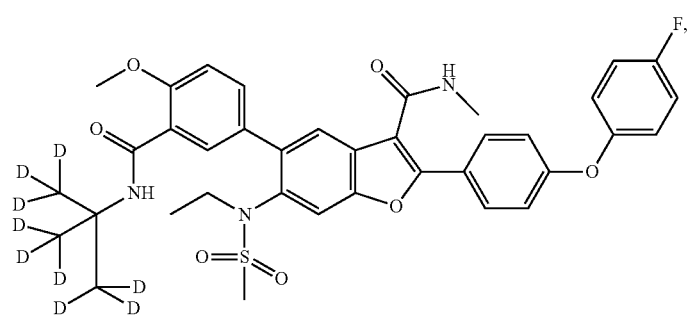

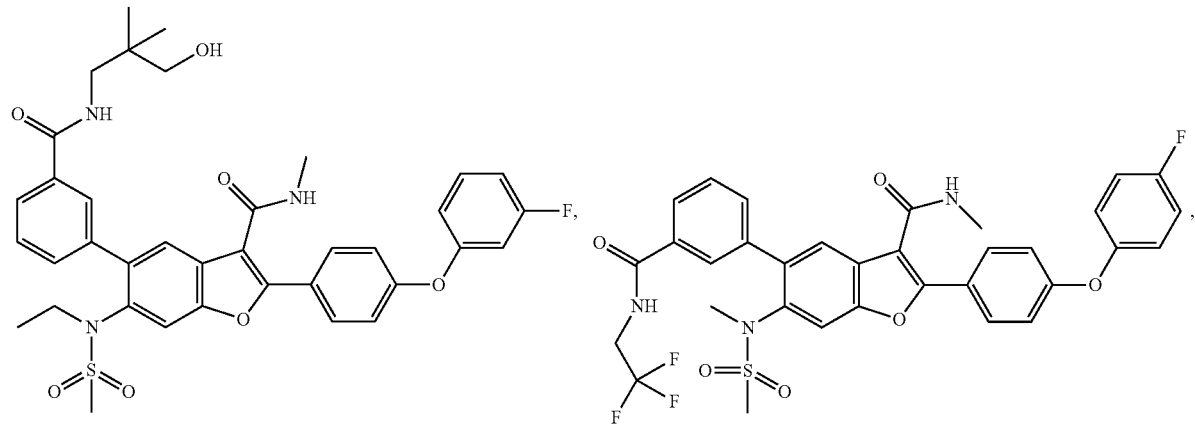
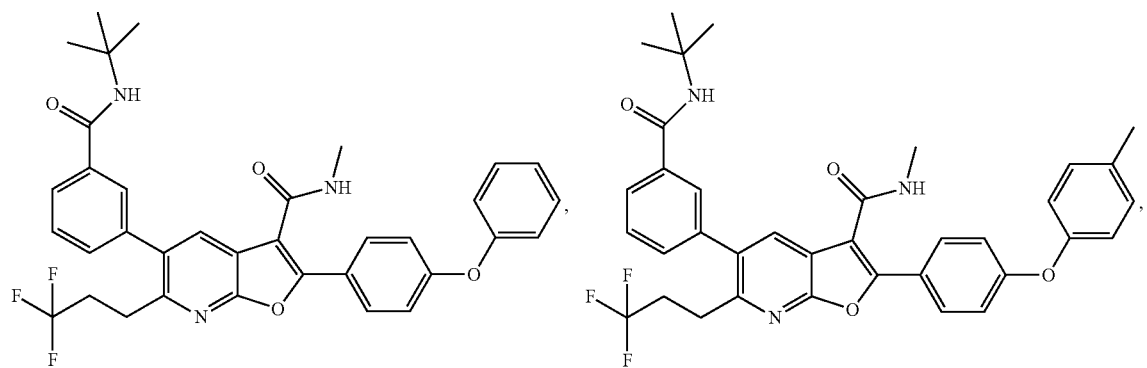
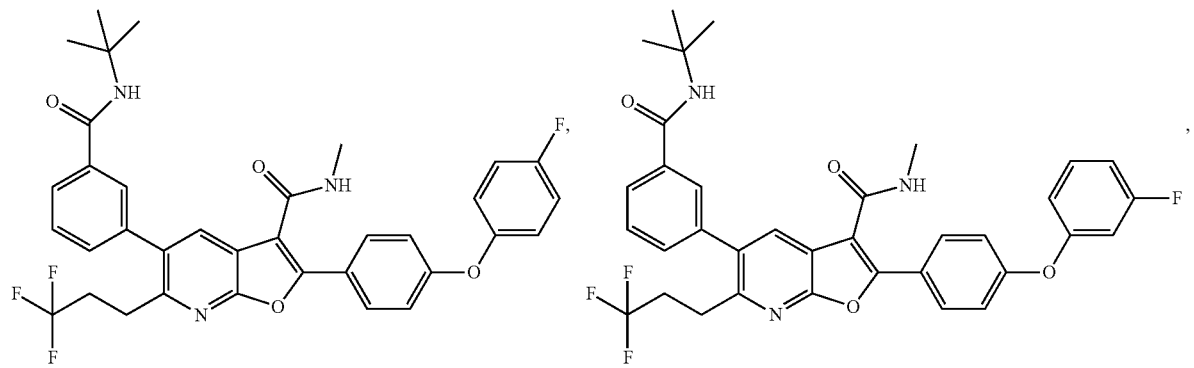
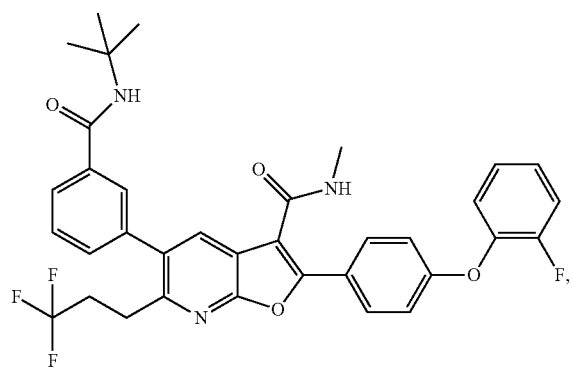

-continued
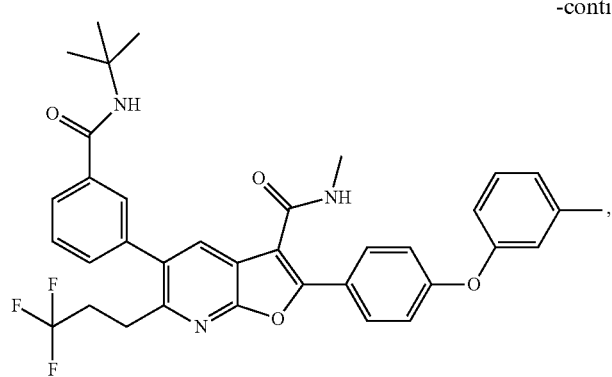
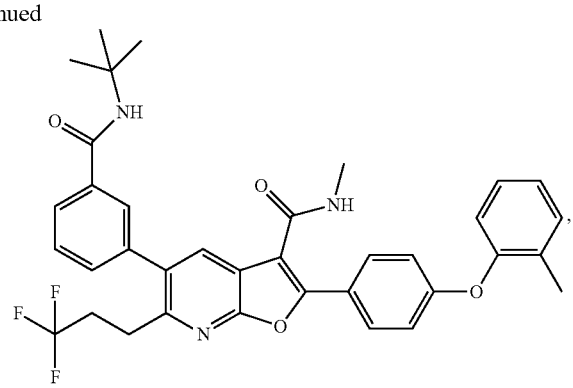
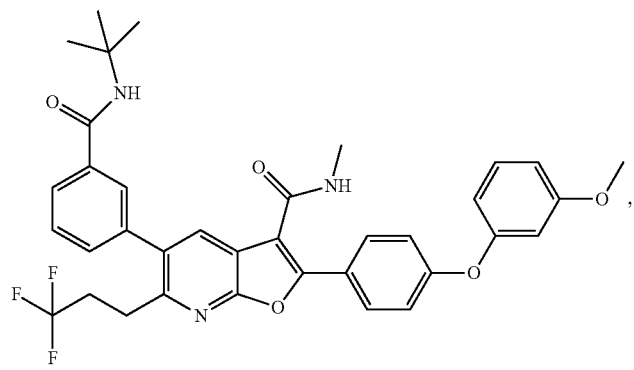
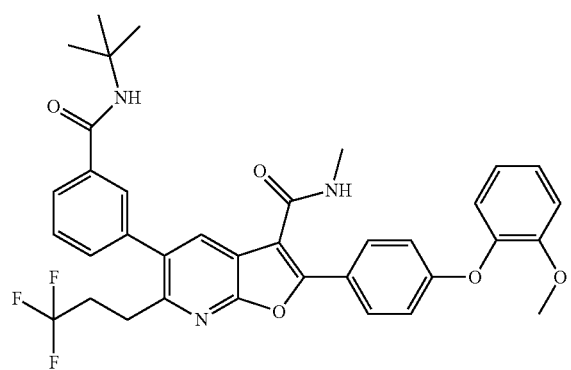
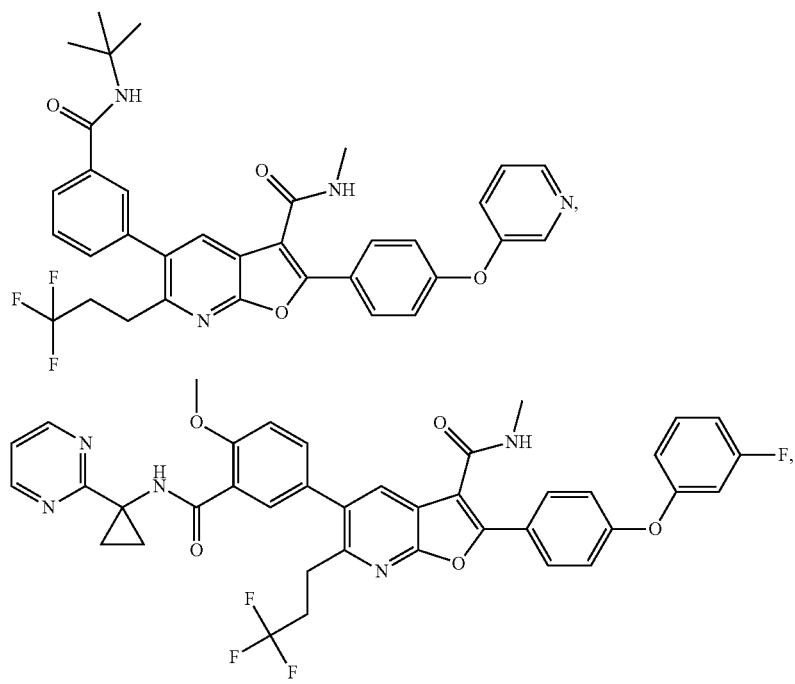

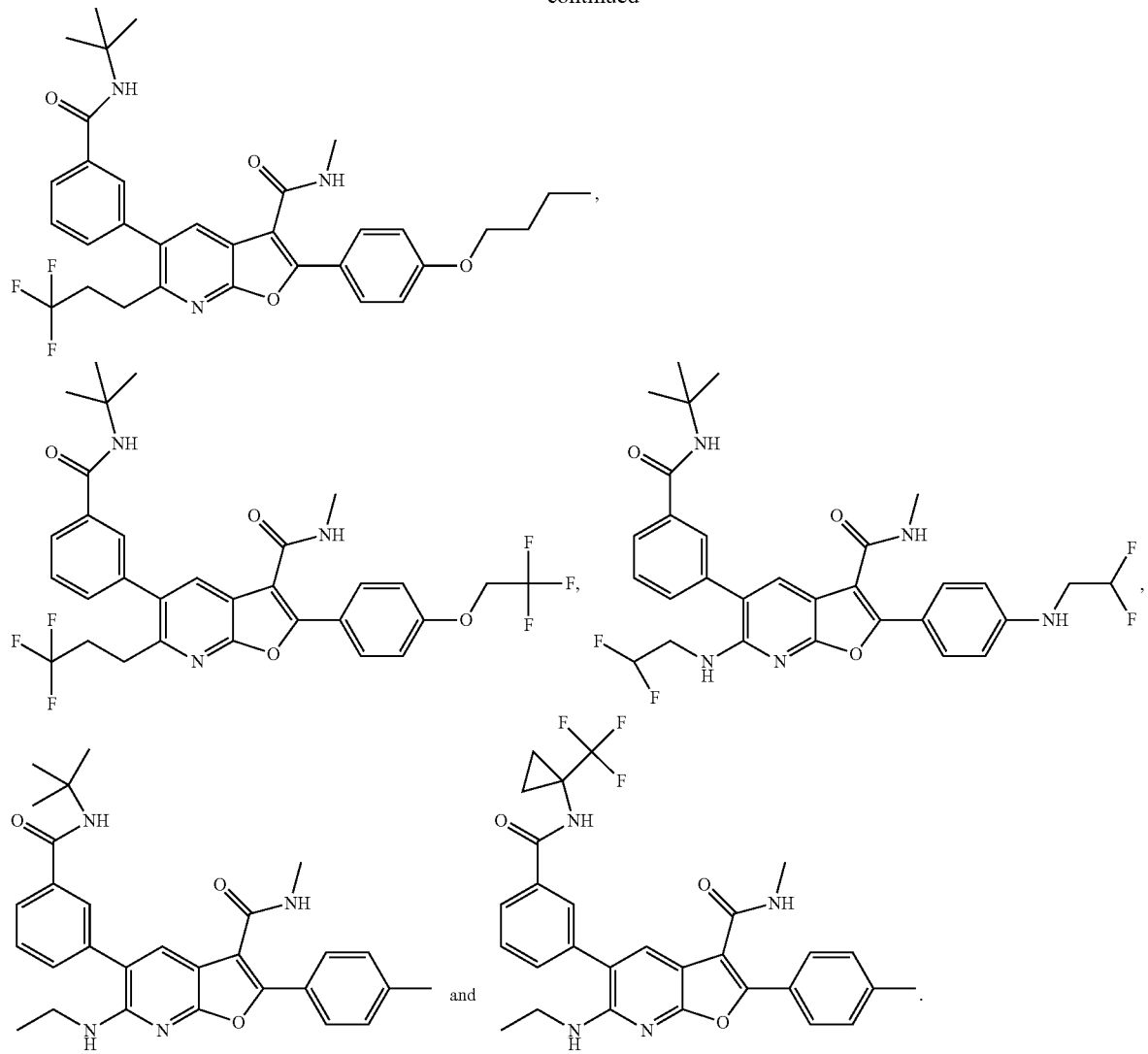

Pharmaceutical Compositions and Methods of Treatment

The compounds according to the various embodiments herein set forth demonstrate activity against HCV NS5B, and can be useful in treating HCV and HCV infection. Therefore, another aspect of the invention is a composition comprising a compound of Formula I, including a pharmaceutically acceptable salt thereof, and a pharmaceutically acceptable carrier, excipient and/or diluent.

Another aspect of the invention is a composition comprising a compound of Formula I, and further comprising an additional compound having anti-HCV activity.

Another aspect of the invention is a composition where the compound having anti-HCV activity is an interferon or a ribavirin. Another aspect of the invention is wherein the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of Formula I, including a pharmaceutically acceptable salt thereof, a pharmaceutically acceptable carrier, excipient, and/or diluent, an interferon and ribavirin.

Another aspect of the invention is a method of inhibiting the function of the HCV replicon comprising contacting the HCV replicon with a compound of Formula I or a pharmaceutically acceptable salt thereof.

Another aspect of the invention is a method of inhibiting the function of the HCV NS5B protein comprising contacting the HCV NS5B protein with a compound of Formula I or a pharmaceutically acceptable salt thereof.

Another aspect of the invention is a method of treating an HCV infection in a patient comprising administering to the patient a therapeutically effective amount of a compound of Formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of Formula I, including a pharmaceutically acceptable salt thereof, in conjunction with (prior to, after, or concurrently) another compound having anti-HCV activity.

Another aspect of the invention is the method wherein the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method wherein the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method wherein the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection. In some embodiments, "therapeutically effective" can mean the amount which will ameliorate or reduce the HCV infection, and/or the effects thereof, or in certain other embodiments, completely eliminate the infection itself.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients and/or diluents. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is about 0.25-1000 mg/unit.

Liquid compositions are usually in dosage unit ranges. Generally, the liquid composition will be in a unit dosage range of about 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other agents used clinically. Typically, the daily dose will be about 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of about 1-100 mg/kg body weight daily in conjunction with other agents. The other agents generally will be given in the amounts used therapeutically. The specific dosing regimen, however, will be determined by a physician using sound medical judgment.

Some examples of compounds suitable for compositions and methods are listed in Table 1.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |

TABLE 1-continued

| Brand Name | Physiological Class | Type of Inhibitor or Target | Source Company |
|---|---|---|---|
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |

TABLE 1-continued

| Brand Name | Physiological Class | Type of Inhibitor or Target | Source Company |
|---|---|---|---|
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |

TABLE 1-continued

| Brand Name | Physiological Class | Type of Inhibitor or Target | Source Company |
|---|---|---|---|
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lambda | Antiviral | Interferon | ZymoGenetics/Bristol-Myers Squibb |

Synthesis Methods

The compounds may be made by methods available to the skilled artisan, including those described below. Some reagents and intermediates are available in the art. Other reagents and intermediates can be made by methods available to the skilled artisan using commercially available materials. The variables (e.g. numbered "R" substituents) used to describe the synthesis of the compounds are intended only to illustrate how to make these compounds, and are not to be confused with variables used in the claims or in other sections of the specification.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "TEA" for triethylamine.

For the section of compounds in the 0000 series all Liquid Chromatography (LC) data were recorded on a Shimadzu LC-10AS or LC-20AS liquid chromatograph using a SPD-10AV or SPD-20A UV-Vis detector and Mass Spectrometry (MS) data were determined with a Micromass Platform for LC in electrospray mode.

HPLC Method (i.e., Compound Isolation).

Compounds purified by preparative HPLC were diluted in methanol (1.2 mL) and purified using a Shimadzu LC-8A or LC-10A or Dionex APS-3000 or Waters Acquity™ automated preparative HPLC system.

EXAMPLES

Preparation of Compounds 1001 and 1002

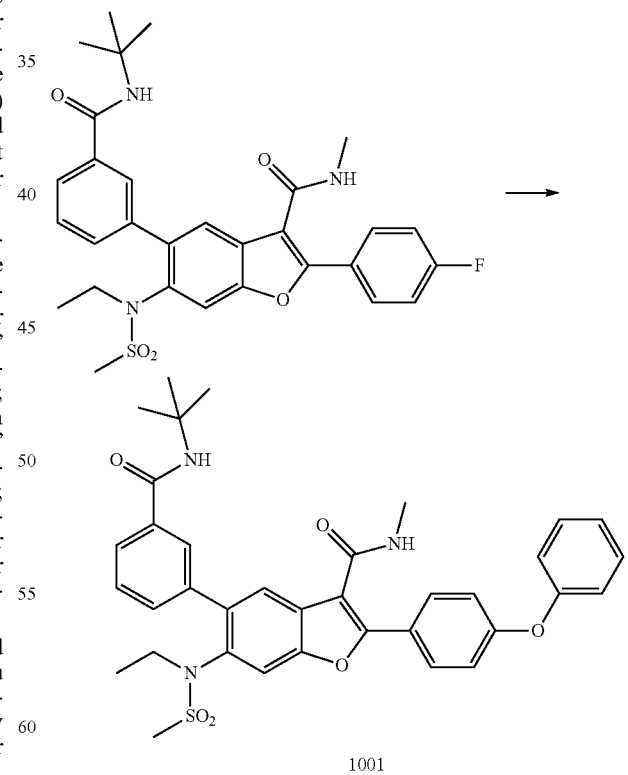

To a solution of phenol (49.9 mg) and sodium hydride (21.21 mg) in DMF (2 mL) was added 5-(3-(tert-butylcarbamoyl)phenyl)-6-(N-ethylmethylsulfonamido)-2-(4-fluorophenyl)-N-methylbenzofuran-3-carboxamide (15 mg). The mixture was heated to 85° C. for 16 hours. The reaction was quenched with 5% NaHCO₃ aqueous solution and extracted with EtOAc. The organic layer was washed with brine and concentrated to give a residue which was purified by preparative HPLC system.

| 1001 | |
|---|---|
| MS (M + H)⁺ Calcd. | 640.2 |
| MS (M + H)⁺ Observ. | 640.3 |
| Retention Time | 1.81 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Compound 1002 was prepared via the same procedure as for compound 1001, using the corresponding phenol. LC condition for compound 1002 was the same for compound 1001.

| Cmpd # | Structure | MS (M + H)⁺ Calcd. | MS (M + H)⁺ Observ. | Retention Time (min) |
|---|---|---|---|---|
| 1002 | 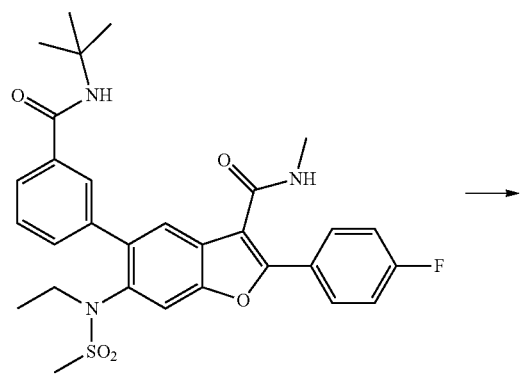 | 658.2 | 658.3 | 1.83 |

Preparation of Compounds 1003-1007

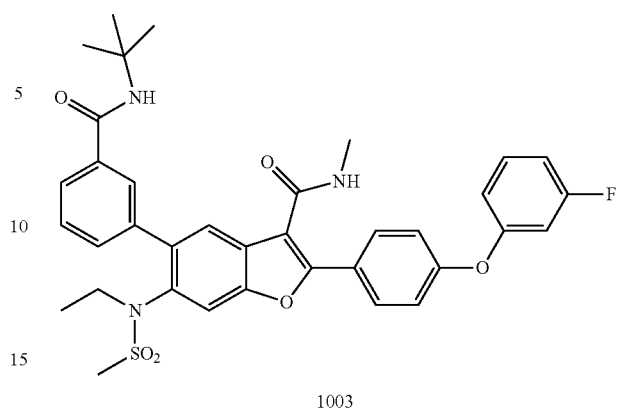

1003

A mixture of 5-(3-(tert-butylcarbamoyl)phenyl)-6-(N-ethylmethylsulfonamido)-2-(4-fluorophenyl)-N-methylbenzofuran-3-carboxamide (10 mg), 3-fluorophenol (59.5 mg), K₂CO₃ (9.77 mg) and Cu(0) (2.25 mg) in a sealed tube was heated to 140° C. for 16 hours. The mixture was diluted with DMF and filtered to removed solid. The solution of the mixture was purified by preparative HPLC system.

Compounds 1004-1007 were prepared via the same procedure as for compound 1001, using the corresponding phenol. LC condition for compounds 1004-1007 was the same for compound 1003.

| LC Condition | |
|---|---|
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

| Cmpd # | Structure | MS (M + H)+ Calcd. | MS (M + H)+ Observ. | Retention Time (min) |
|---|---|---|---|---|
| 1003 | 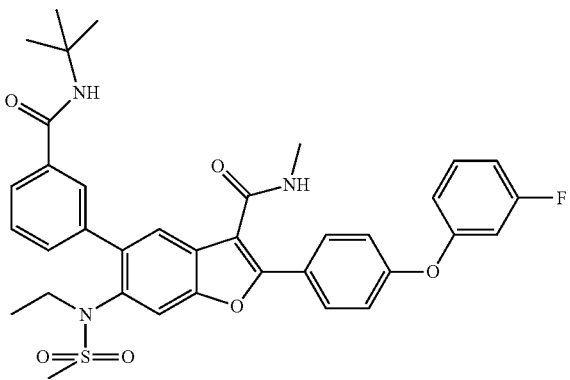 [SMILES: CCN(c1cc2oc(-c3ccc(Oc4cccc(F)c4)cc3)c(C(=O)NC)c2cc1-c1cccc(C(=O)NC(C)(C)C)c1)S(C)(=O)=O] | 658.2 | 658.2 | 1.87 |
| 1004 | 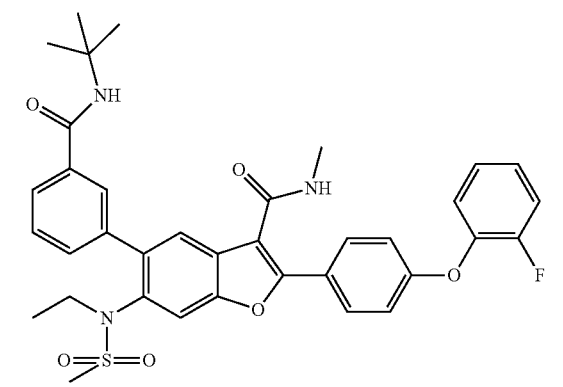 [SMILES: CCN(c1cc2oc(-c3ccc(Oc4ccccc4F)cc3)c(C(=O)NC)c2cc1-c1cccc(C(=O)NC(C)(C)C)c1)S(C)(=O)=O] | 658.2 | 658.2 | 1.78 |
| 1005 | 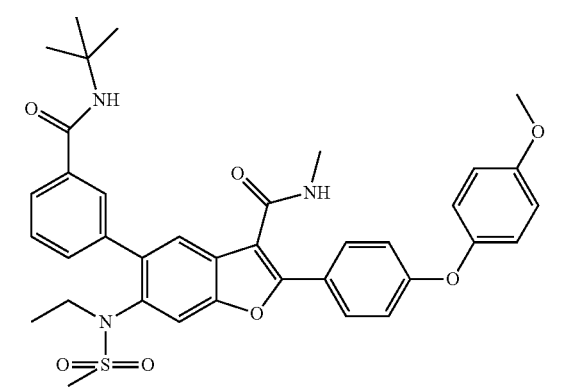 | 670.3 | 670.2 | 1.80 |
| 1006 | 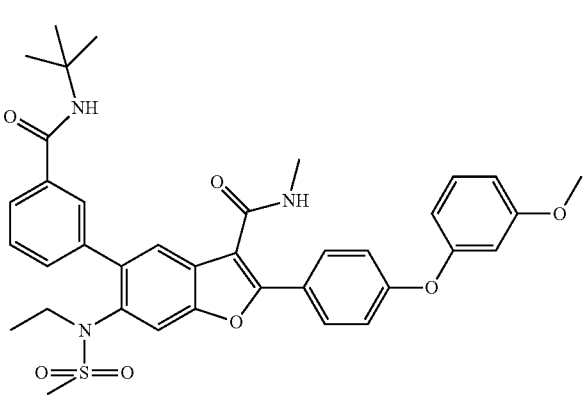 [SMILES: CCN(c1cc2oc(-c3ccc(Oc4cccc(OC)c4)cc3)c(C(=O)NC)c2cc1-c1cccc(C(=O)NC(C)(C)C)c1)S(C)(=O)=O] | 670.3 | 670.2 | 1.84 |

-continued

| Cmpd # | Structure | MS (M + H)+ Calcd. | MS (M + H)+ Observ. | Retention Time (min) |
|---|---|---|---|---|
| 1007 | 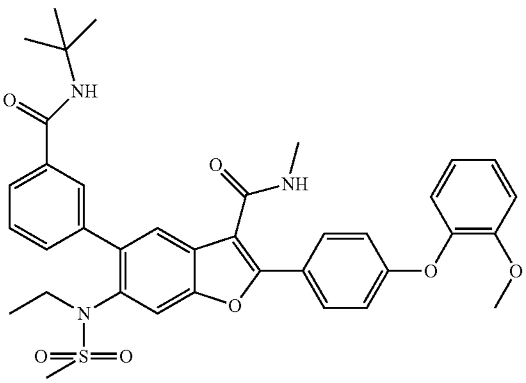 [SMILES: CCN(c1cc2oc(-c3ccc(Oc4ccccc4OC)cc3)c(C(=O)NC)c2cc1-c1cccc(C(=O)NC(C)(C)C)c1)S(C)(=O)=O] | 670.3 | 670.2 | 1.73 |

Preparation of Compound 1008

|  | 1008 |
|---|---|
| MS (M + H)+ Calcd. | 568.2 |
| MS (M + H)+ Observ. | 568.2 |
| Retention Time | 1.94 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water - Methanol-FA |
| Column | PHENOMENEX-LUNA 2.0 × 30 mm 3 um |

To a mixture of 3-fluorophenol (66.6 mg) and NaH (31.7 mg) in DMF (2 mL) was added 5-(3-(bicyclo[1.1.1]pentan-1-ylcarbamoyl)-4-methoxyphenyl)-6-(diethylamino)-2-(4-fluorophenyl)-N-methylbenzofuran-3-carboxamide (11 mg). The mixture was heated to 85° C. for 16 hours. The reaction was quenched with 5% NaHCO₃ aqueous solution and extracted with EtOAc (2×50 mL). The organic layers were combined and washed with brine, dried over MgSO₄ and concentrated. The residue was purified by preparative HPLC system.

Preparation of Compounds 1011, 1014, 1015, 2001-2003, 2005, 3002 and 6001

Compounds 1011, 1014, 1015, 2001-2003, 2005, 3002 and 6001 were prepared via the same procedure as for compound 1008, using the corresponding fluoro derivative and alcohol or carbon nucleophile.

| LC Condition | |
|---|---|
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

| Cmpd # | Reaction | Product MS (M + H)+ Calcd. | Product MS (M + H)+ Observ. | Product Retention Time (min) |
|---|---|---|---|---|
| 1011 | | 666.3 | 666.2 | 1.73 |
| 1014 | | 436.1 | 436.0 | 2.19 |
| 1015 | | 656.2 | 656.2 | 1.92 |

| Cmpd # | Reaction | Product MS (M + H)+ Calcd. | Product MS (M + H)+ Observ. | Product Retention Time (min) |
|---|---|---|---|---|
| | 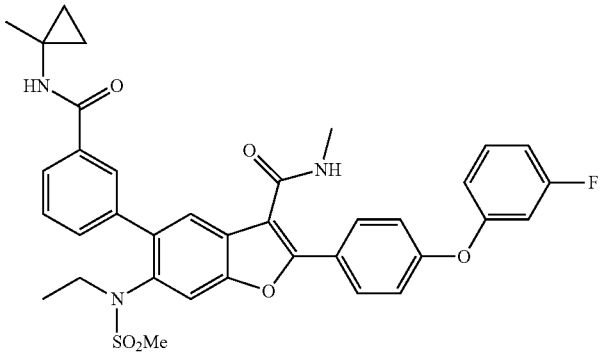 1015 | | | |
| 2001 | 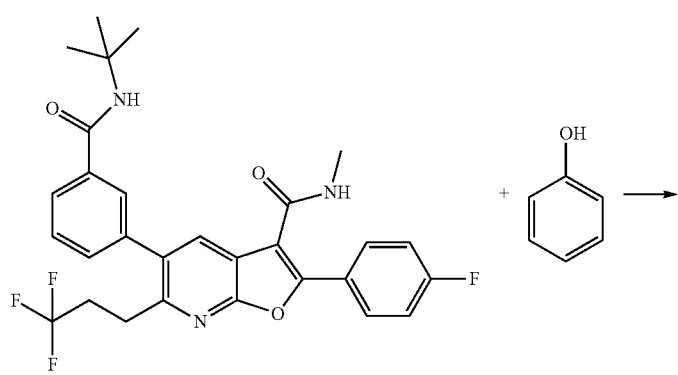 | 616.2 | 616.2 | 2.14 |
| | 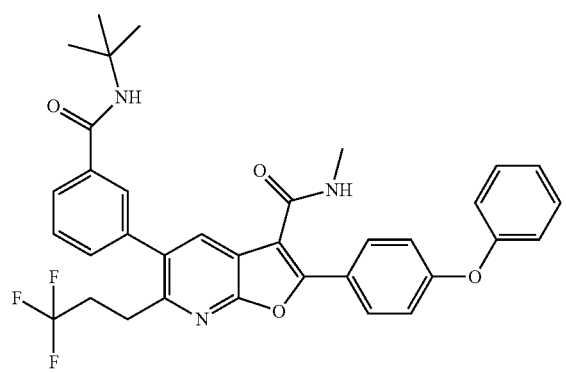 2001 | | | |

-continued

| Cmpd # | Reaction | Product MS (M + H)+ Calcd. | Product MS (M + H)+ Observ. | Product Retention Time (min) |
|---|---|---|---|---|
| 2002 | | 630.3 | 630.2 | 2.23 |
| 2003 | | 646.3 | 646.2 | 2.11 |

-continued

| Cmpd # | Reaction | Product MS (M + H)+ Calcd. | Product MS (M + H)+ Observ. | Product Retention Time (min) |
|---|---|---|---|---|
| 2005 | | 634.2 | 634.2 | 2.19 |
| 3002 | | 622.2 | 622.2 | 1.93 |

| Cmpd # | Reaction | Product MS (M + H)+ Calcd. | Product MS (M + H)+ Observ. | Product Retention Time (min) |
|---|---|---|---|---|
| | 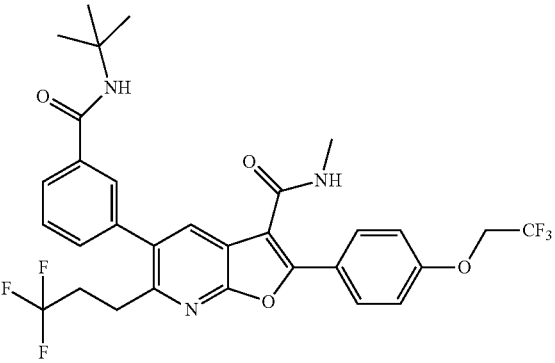<br>3002 | | | |
| 6001 | 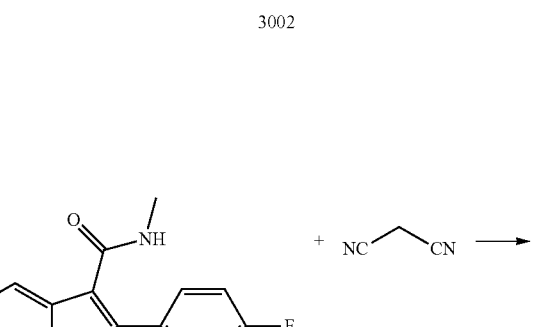<br>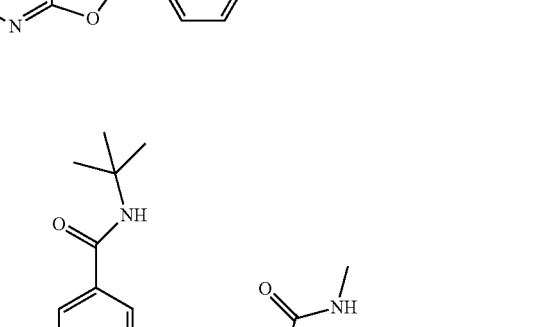<br>6001 | 606.2 | 606.2 | 1.66 |

Preparation of Compounds 1016-1027

Compounds 1016-1027 were prepared via the same procedure as was compound 1008, using the corresponding fluoro derivative and phenol.

| LC Condition | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

| Cmpd # | Reaction | Product MS (M + H)+ Calcd. | Product MS (M + H)+ Observ. | Product Retention Time (min) |
| --- | --- | --- | --- | --- |
| 1016 | 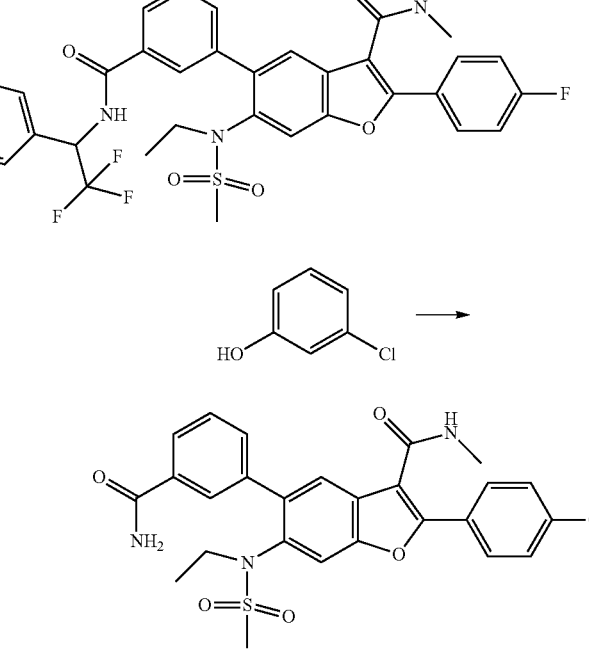 | 618.1 | 618.1 | 2.23 |
| 1017 | 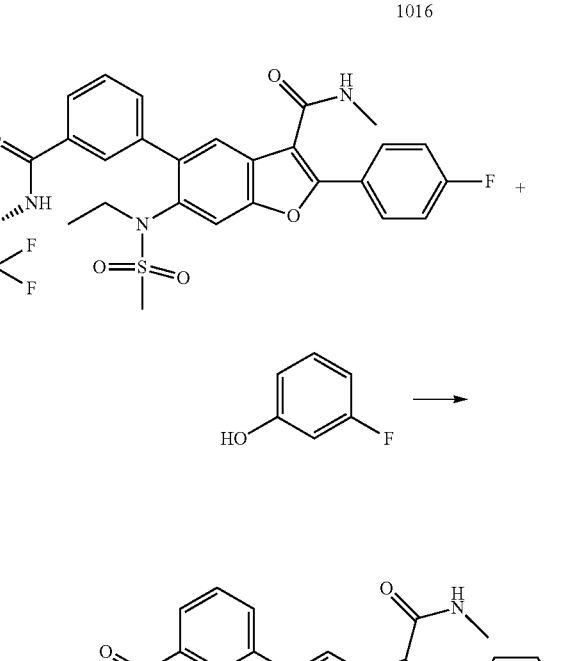 | 698.2 | 698.3 | 2.31 |

| Cmpd # | Reaction | Product MS (M + H)+ Calcd. | Product MS (M + H)+ Observ. | Product Retention Time (min) |
|---|---|---|---|---|
| 1018 | 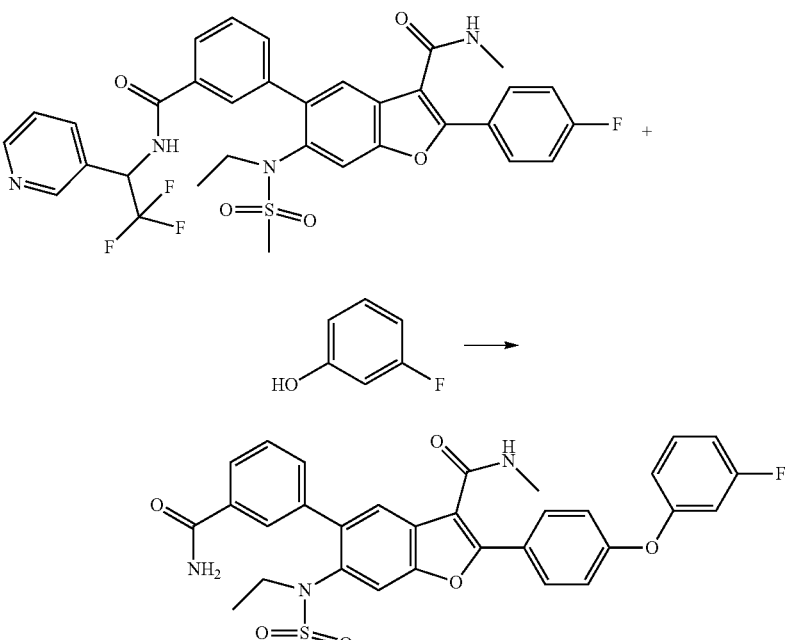 | 602.2 | 602.2 | 2.12 |
| 1019 | 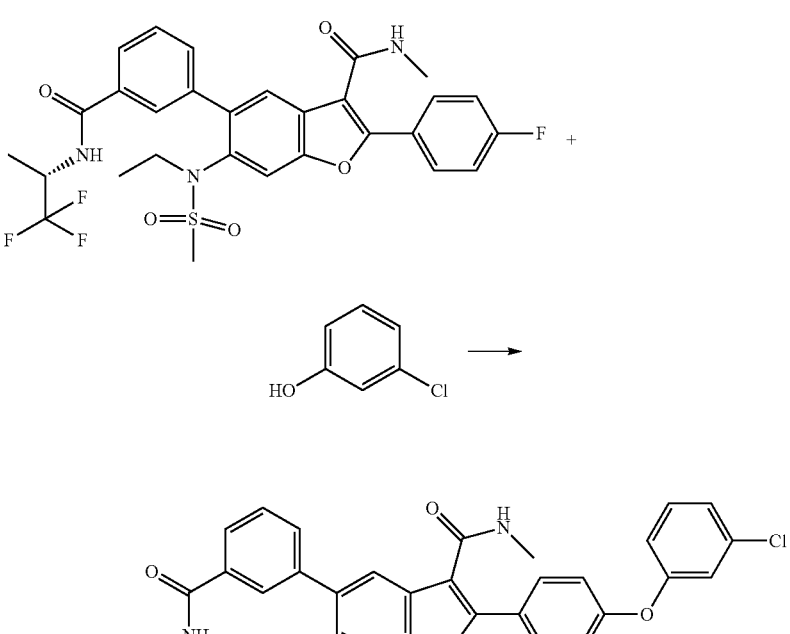 | 714.2 | 714.2 | 2.45 |

| Cmpd # | Reaction | Product MS (M + H)+ Calcd. | Product MS (M + H)+ Observ. | Product Retention Time (min) |
|---|---|---|---|---|
| 1020 | | 670.2 | 670.2 | 2.25 |
| 1021 | | 697.3 | 697.4 | 2.34 |

| Cmpd # | Reaction | Product MS (M + H)+ Calcd. | Product MS (M + H)+ Observ. | Product Retention Time (min) |
|---|---|---|---|---|
| 1022 | 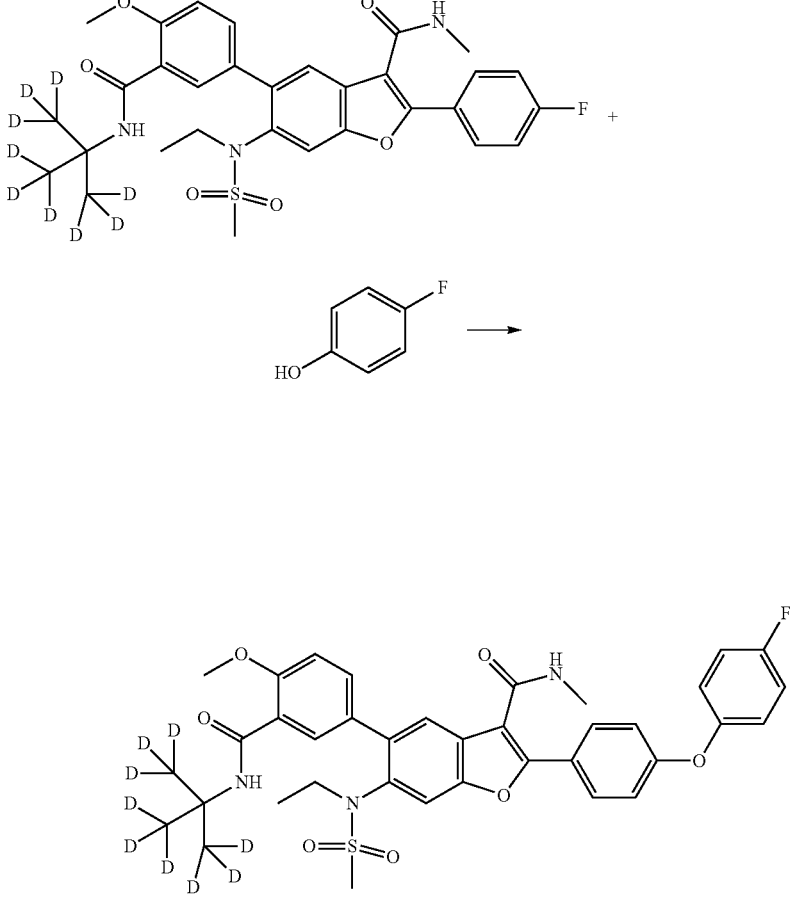 | 697.3 | 697.4 | 2.32 |
| 1023 | 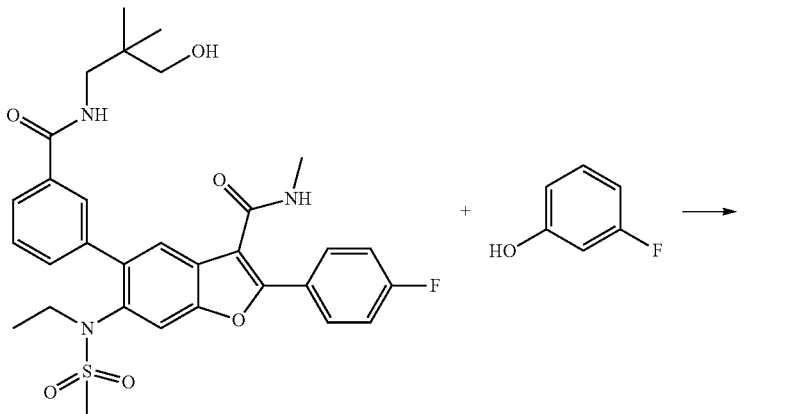 [SMILES: CCN(c1cc2oc(-c3ccc(F)cc3)c(C(=O)NC)c2cc1-c1cccc(C(=O)NCC(C)(C)CO)c1)S(C)(=O)=O ; Oc1cccc(F)c1] | 688.2 | 688.3 | 2.26 |

-continued

| Cmpd # | Reaction | Product MS (M + H)+ Calcd. | Product MS (M + H)+ Observ. | Product Retention Time (min) |
|---|---|---|---|---|
| | 1023 | | | |
| 1024 | 1024 | 746.2 | 746.4 | 2.14 |
| 1025 | | 746.2 | 746.4 | 2.14 |

-continued

| Cmpd # | Reaction | Product MS (M + H)+ Calcd. | Product MS (M + H)+ Observ. | Product Retention Time (min) |
|---|---|---|---|---|
| 1025 | | | | |
| 1026 | | 670.2 | 670.2 | 2.20 |
| 1027 | | 602.2 | 602.2 | 2.14 |

| Cmpd # | Reaction | Product MS (M + H)+ Calcd. | Product MS (M + H)+ Observ. | Product Retention Time (min) |
|---|---|---|---|---|
| 1027 | 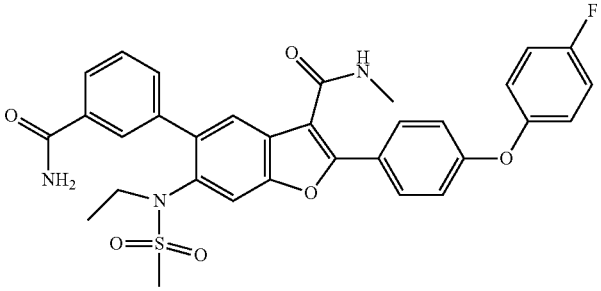 | | | |

Preparation of Compounds 1009 and 1010

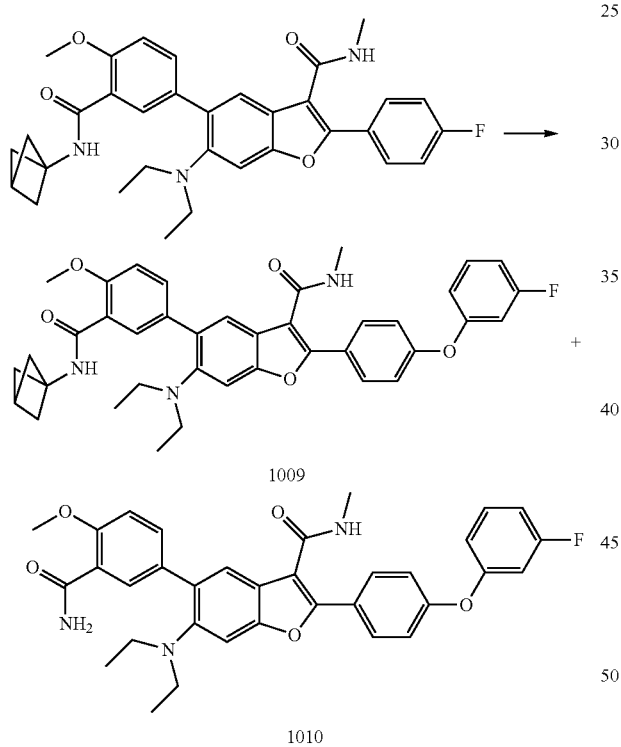

A mixture of 3-fluorophenol (91 mg), 5-(3-(bicyclo[1.1.1]pentan-1-ylcarbamoyl)-4-methoxyphenyl)-6-(diethylamino)-2-(4-fluorophenyl)-N-methylbenzofuran-3-carboxamide (15 mg), K$_2$CO$_3$ (14.92 mg) and Cu(0) (3.43 mg) was heated to 140° C. for 16 hours. The products were isolated by preparative HPLC system.

| 1009 | |
|---|---|
| MS (M + H)+ Calcd. | 648.3 |
| MS (M + H)+ Observ. | 648.2 |
| Retention Time | 2.30 min |

| 1010 | |
|---|---|
| MS (M + H)+ Calcd. | 582.2 |
| MS (M + H)+ Observ. | 582.2 |
| Retention Time | 2.06 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Preparation of Compounds 1012, 1013, 2004, 2006-2014, 3001, 4001 and 5001

Compounds 1012, 1013, 2004, 2006-2014, 3001, 4001 and 5001 were prepared via the same procedure as for compounds 1009/1010, using the corresponding fluoro derivative and alcohol or amine or thiol.

| LC Condition | |
|---|---|
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

| Cmpd # | Reaction | Product MS (M + H)+ Calcd. | Product MS (M + H)+ Observ. | Product Retention Time (min) |
|---|---|---|---|---|
| 1012 | 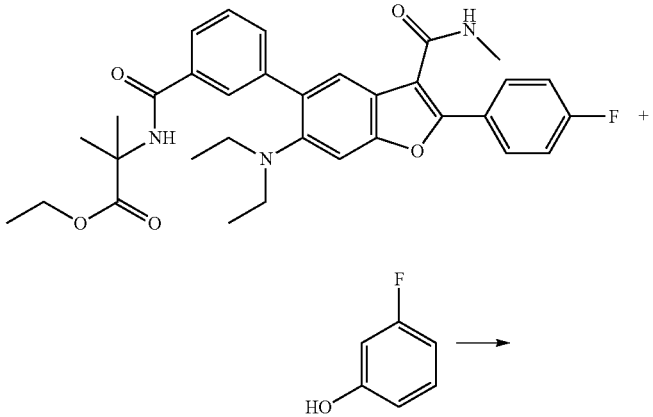 | 638.3 | 638.3 | 1.36 |
| 1013 | 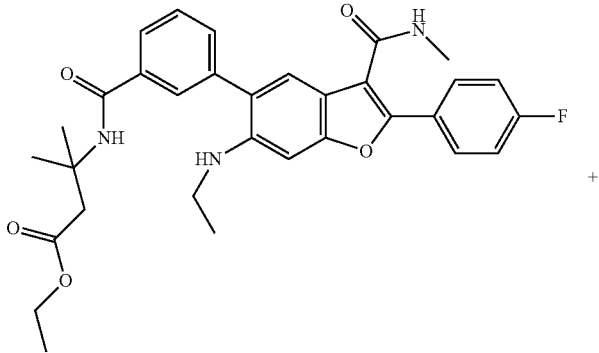 [SMILES: CCNc1cc2oc(-c3ccc(F)cc3)c(C(=O)NC)c2cc1-c1cccc(C(=O)NC(C)(C)CC(=O)OCC)c1] | 624.2 | 624.2 | 1.96 |

| Cmpd # | Reaction | Product MS (M + H)+ Calcd. | Product MS (M + H)+ Observ. | Product Retention Time (min) |
|---|---|---|---|---|
| 1013 | | | | |
| 2004 | | 634.2 | 634.2 | 2.14 |
| 2006 | | 634.2 | 634.2 | 2.11 |

| Cmpd # | Reaction | Product MS (M + H)+ Calcd. | Product MS (M + H)+ Observ. | Product Retention Time (min) |
|---|---|---|---|---|
| 2007 | | 630.3 | 630.2 | 2.25 |
| 2008 | | 630.3 | 630.2 | 2.26 |

| Cmpd # | Reaction | Product MS (M + H)+ Calcd. | Product MS (M + H)+ Observ. | Product Retention Time (min) |
|---|---|---|---|---|
| | 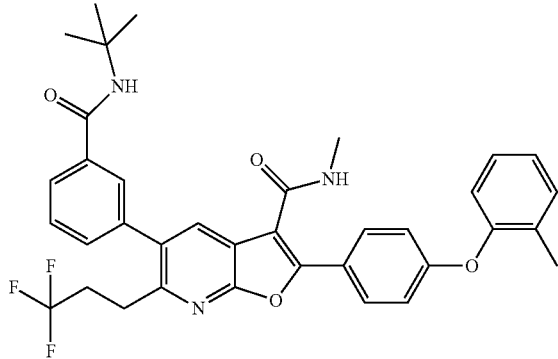 2008 | | | |
| 2009 | 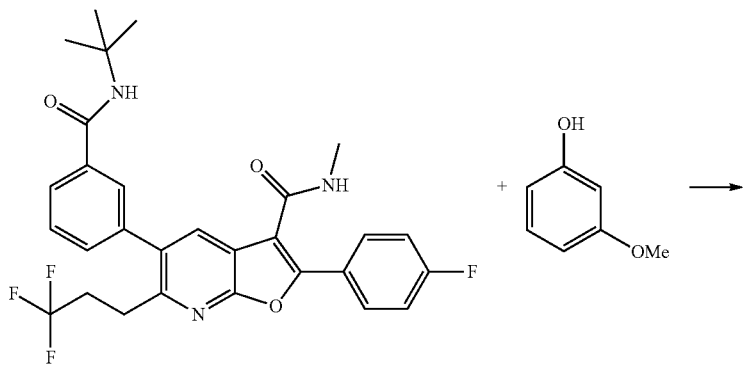 [SMILES: CNC(=O)c1c(-c2ccc(F)cc2)oc2nc(CCC(F)(F)F)c(-c3cccc(C(=O)NC(C)(C)C)c3)cc12 ; COc1cccc(O)c1] | 646.3 | 646.2 | 2.46 |
| | 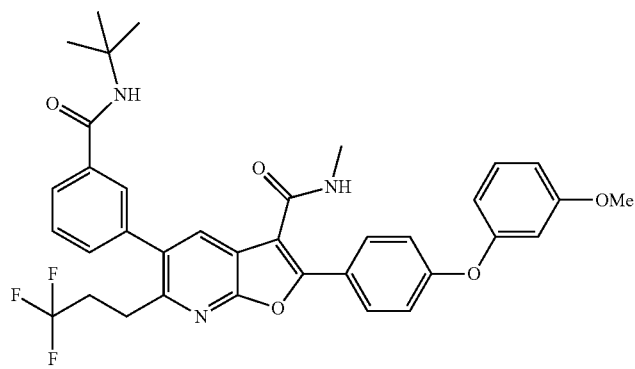 2009 | | | |

-continued
| Cmpd # | Reaction | Product MS (M + H)+ Calcd. | Product MS (M + H)+ Observ. | Product Retention Time (min) |
|---|---|---|---|---|
| 2010 | 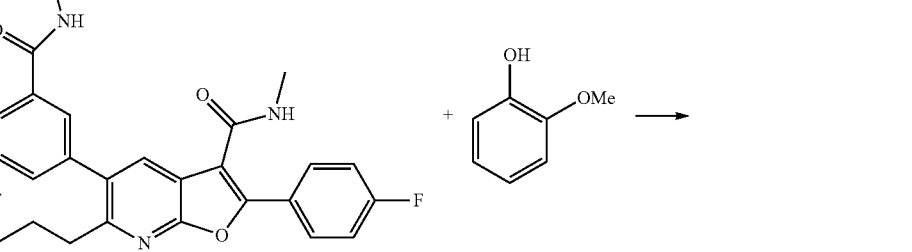 | 646.3 | 646.2 | 2.06 |
| 2011 | 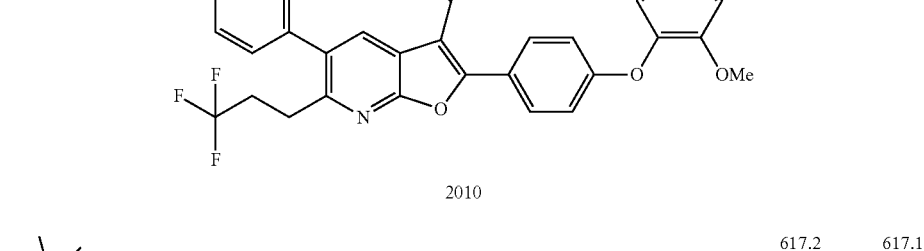 | 617.2 | 617.1 | 1.57 |

-continued

| Cmpd # | Reaction | Product MS (M + H)+ Calcd. | Product MS (M + H)+ Observ. | Product Retention Time (min) |
|---|---|---|---|---|
| 2012 | | 617.2 | 617.2 | 1.66 |
| 2013 | | 660.2 | 660.2 | 2.03 |

| Cmpd # | Reaction | Product MS (M + H)+ Calcd. | Product MS (M + H)+ Observ. | Product Retention Time (min) |
|---|---|---|---|---|
| 2014 | | 726.2 | 726.1 | 2.07 |
| 3001 | | 596.3 | 596.2 | 2.19 |

| Cmpd # | Reaction | Product MS (M + H)+ Calcd. | Product MS (M + H)+ Observ. | Product Retention Time (min) |
|---|---|---|---|---|
| | 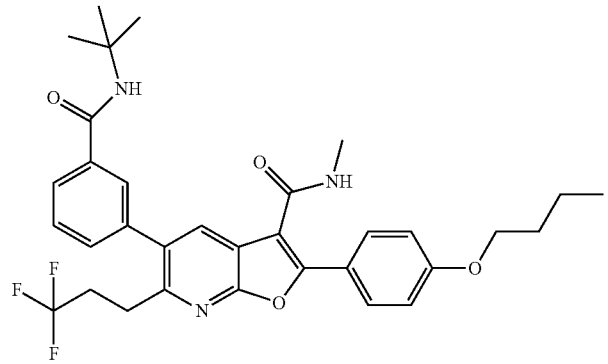 3001 | | | |
| 4001 | 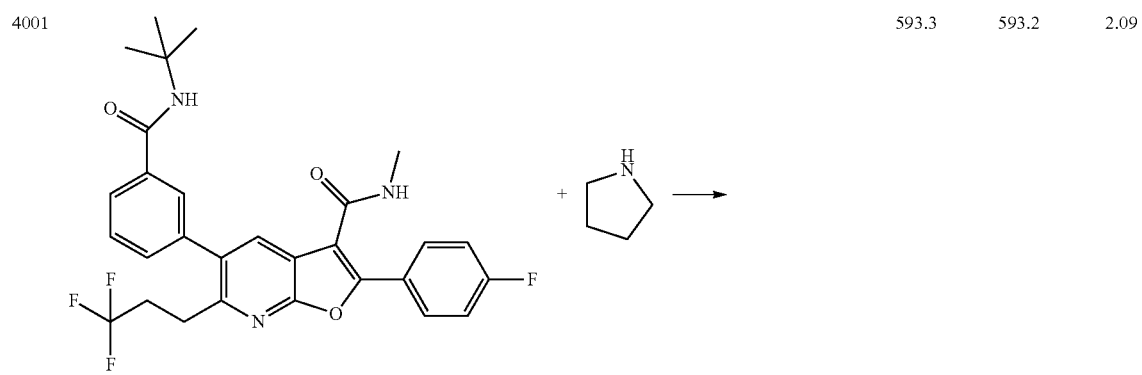 | 593.3 | 593.2 | 2.09 |
| | 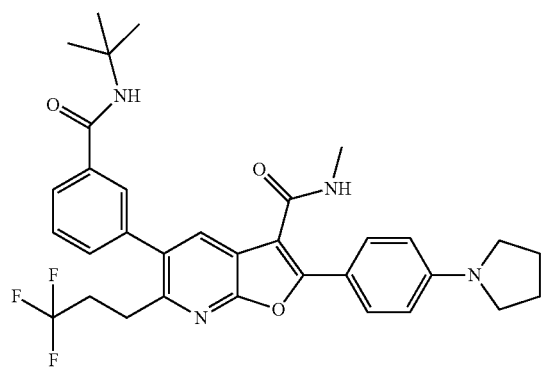 4001 | | | |

| Cmpd # | Reaction | Product MS (M + H)+ Calcd. | Product MS (M + H)+ Observ. | Product Retention Time (min) |
|---|---|---|---|---|
| 5001 | 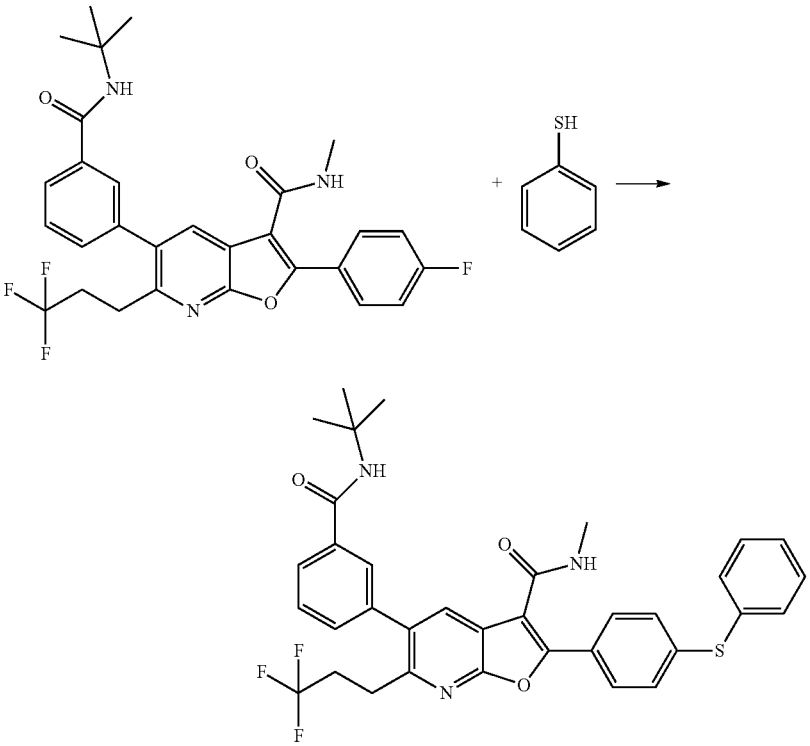 | 632.2 | 632.2 | 2.28 |

Preparation of Compound 4002

Step 1: Preparation of 5-bromo-6-chloro-3-((4-chlorophenyl)ethynyl)pyridin-2-yl acetate

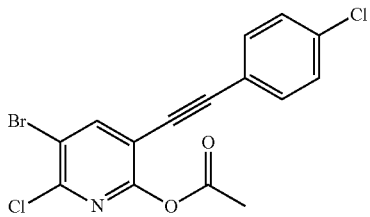 [SMILES: CC(=O)Oc1nc(Cl)c(Br)cc1C#Cc1ccc(Cl)cc1]

5-bromo-6-chloro-3-iodopyridin-2-yl acetate (500 mg, 1.33 mmol) was dissolved in THF (10 mL) and cooled to 0° C. TEA (0.5 mL), copper (I) iodide (18 mg, 0.093 mmol), and bistriphenyl phosphine palladium dichloride (9.3 mg, 0.013 mmol) were added to the reaction mixture. The mixture was degassed and charged with N₂— 3×. Next, 1-chloro-4-ethynylbenzene (218 mg, 1.59 mmol) was added dropwise at 0° C. The reaction mixture was then allowed to slowly warm to rt overnight. LCMS and TLC show the reaction to be complete. The reaction mixture was concentrated and was purified on silica gel (Biotage, EtOAc/hexanes gradient, fraction collection at λ=254 nm) to give the expected product 5-bromo-6-chloro-3-((4-chlorophenyl)ethynyl)pyridin-2-yl acetate (420 mg, 1.09 mmol, 82% yield) consistent by LCMS and NMR. LC-MS retention time: 3.24 min; m/z (MH+): 386. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. 1H NMR (400 MHz, CHLOROFORM-d) δ 8.14 (s, 1H), 7.43-7.35 (m, 4H), 2.39 (s, 3H)

Step 2: Preparation of methyl 5-bromo-6-chloro-2-(4-chlorophenyl)furo[2,3-b]pyridine-3-carboxylate

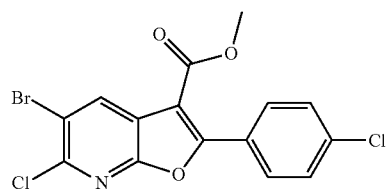 [SMILES: COC(=O)c1c(-c2ccc(Cl)cc2)oc2nc(Cl)c(Br)cc12]

K₂CO₃ (287 mg, 2.08 mmol) was added to a stirring slurry of 5-bromo-6-chloro-3-((4-chlorophenyl)ethynyl)pyridin-2-yl acetate (400 mg, 1.04 mmol) in MeOH (50 mL) at rt. The reaction was allowed to stir for 30 min. A solution resulted. LCMS showed major peak with M+H of 328 and along with TLC indicated the deprotection was complete to give 3-bromo-6-chloro-5-((4-chlorophenyl)ethynyl)pyridin-2(1H)-one. This solution was poured into a parr bomb containing dry palladium(II) chloride (31 mg, 0.17 mmol), sodium acetate (170 mg, 2.08 mmol), copper(II) chloride dihydrate (531 mg, 3.12 mmol). The reaction was charged with CO (300 PSI) minimizing the time the reaction is devoid of CO. The reaction was stirred vigourously overnight at rt. The reaction was concentrated and the mixture was diluted with EtOAc and washed with aq 1M HCl, and sat aq NaCl. The organic phase was dried over Na2SO4, filtered and concentrated and was purified on silica gel (Biotage, EtOAc/hexanes gradient, fraction collection at $\lambda$=254 nm) to give the expected product methyl 5-bromo-6-chloro-2-(4-chlorophenyl)furo[2,3-b]pyridine-3-carboxylate (267 mg, 0.666 mmol, 64.1% yield) consistent by LCMS and NMR. LC-MS retention time: 3.47 min; m/z (MH+): 401. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. 1H NMR (400 MHz, CHLOROFORM-d) $\delta$ 8.58 (s, 1H), 8.14-8.09 (m, 2H), 7.53-7.49 (m, 2H), 4.00 (s, 3H)

Step 3: Preparation of 5-bromo-6-chloro-2-(4-chlorophenyl)furo[2,3-b]pyridine-3-carboxylic acid

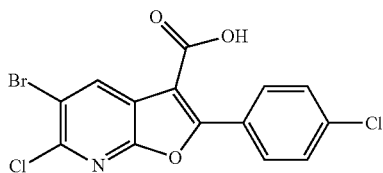 [SMILES: O=C(O)c1c(-c2ccc(Cl)cc2)oc2nc(Cl)c(Br)cc12]

1M aq NaOH (3.3 ml, 3.3 mmol) was added to a stirring solution of methyl 5-bromo-6-chloro-2-(4-chlorophenyl)furo[2,3-b]pyridine-3-carboxylate (267 mg, 0.666 mmol) in MeOH (3.3 ml), THF (3.3 ml) at 65° C. The reaction was allowed to stir for 1 hr. The mixture was diluted with EtOAc and washed with 1M aq HCl, and sat aq NaCl. The organic phase was dried over Na2SO4, filtered and concentrated, azeotroping with toluene, to give the expected product 5-bromo-6-chloro-2-(4-chlorophenyl)furo[2,3-b]pyridine-3-carboxylic acid (250 mg, 0.646 mmol, 97% yield) consistent by LCMS. LC-MS retention time: 2.75 min; m/z (MH+): 388. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode.

Step 4: Preparation of 5-bromo-6-chloro-2-(4-chlorophenyl)-N-methylfuro[2,3-b]pyridine-3-carboxamide

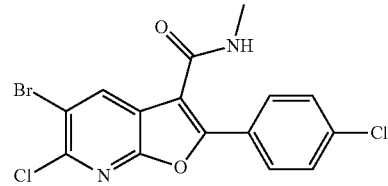 [SMILES: CNC(=O)c1c(-c2ccc(Cl)cc2)oc2nc(Cl)c(Br)cc12]

HATU (368 mg, 0.969 mmol) was added to a stirring solution of 5-bromo-6-chloro-2-(4-chlorophenyl)furo[2,3-b]pyridine-3-carboxylic acid (250 mg, 0.646 mmol), DIEA (338 µl, 1.94 mmol), methanamine hydrochloride (218 mg, 3.23 mmol) in DMF (6.5 ml) at rt. The reaction was allowed to stir for 1 hr then was concentrated and was purified on silica gel (Biotage, MeOH/DCM gradient, fraction collection at $\lambda$=254 nm) to give the expected product 5-bromo-6-chloro-2-(4-chlorophenyl)-N-methylfuro[2,3-b]pyridine-3-carboxamide (229 mg, 0.572 mmol, 89% yield) consistent by LCMS and NMR. LC-MS retention time: 3.02 min; m/z (MH+): 401. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. 1H NMR (400 MHz, CHLOROFORM-d) $\delta$ 8.51 (s, 1H), 7.88-7.80 (m, 2H), 7.57-7.49 (m, 2H), 5.84-5.74 (m, 1H), 3.01 (d, J=5.0 Hz, 3H)

Step 5: Preparation of 3-(6-chloro-2-(4-chlorophenyl)-3-(methylcarbamoyl)furo[2,3-b]pyridin-5-yl)benzoic acid

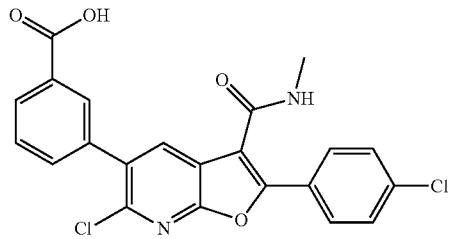 [SMILES: CNC(=O)c1c(-c2ccc(Cl)cc2)oc2nc(Cl)c(-c3cccc(C(=O)O)c3)cc12]

A mixture of 5-bromo-6-chloro-2-(4-chlorophenyl)-N-methylfuro[2,3-b]pyridine-3-carboxamide (215 mg, 0.537 mmol), 3-(4,4,5,5-tetramethyl-1,3,2-dioxaborolan-2-yl)benzoic acid (140 mg, 0.564 mmol), Pd(Ph3P)4 (62 mg, 0.054 mmol) and cesium carbonate (263 mg, 0.806 mmol) was degassed, backfilled with N2 and diluted with water (0.5 ml)

and DMF (5 ml). The mixture was degassed and heated to 60° C. under N2. The reaction was allowed to stir overnight 16 h. LCMS showed ~30% sm remained. An additional 0.3 equiv of 3-(4,4,5,5-tetramethyl-1,3,2-dioxaborolan-2-yl) benzoic acid and 0.03 equiv of Pd(Ph3P)4 was added and the reaction was stirred at 70° C. LCMS in 1 hr showed sm was consumed. The mixture was diluted with EtOAc and washed with aq 1M HCl, and sat aq NaCl. The organic phase was dried over Na2SO4, filtered and concentrated. The material was triturated with DCM to give a yellow solid, the expected product 3-(6-chloro-2-(4-chlorophenyl)-3-(methylcarbamoyl)furo[2,3-b]pyridin-5-yl)benzoic acid (219 mg, 0.496 mmol, 92% yield) crude consistent by LCMS and NMR. LC-MS retention time: 2.57 min; m/z (MH+): 470. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. 1H NMR (400 MHz, DMSO-d6) δ 13.18 (br. s., 1H), 8.62-8.53 (m, 1H), 8.22 (s, 1H), 8.10-7.98 (m, 4H), 7.83-7.78 (m, 1H), 7.69-7.63 (m, 3H), 2.82 (d, J=4.8 Hz, 3H)

Step 6: Preparation of 5-(3-(tert-butylcarbamoyl)phenyl)-6-chloro-2-(4-chlorophenyl)-N-methylfuro[2,3-b]pyridine-3-carboxamide

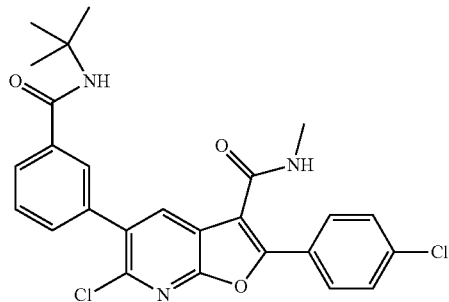 [SMILES: CNC(=O)c1c(-c2ccc(Cl)cc2)oc2nc(Cl)c(-c3cccc(C(=O)NC(C)(C)C)c3)cc12]

3-(6-chloro-2-(4-chlorophenyl)-3-(methylcarbamoyl)furo[2,3-b]pyridin-5-yl)benzoic acid (100 mg, 0.227 mmol) was taken up in DMF (2.3 ml) and treated with N-ethyl-N-isopropylpropan-2-amine (119 μl, 0.680 mmol), 2-methylpropan-2-amine (64 μl, 0.68 mmol) followed by 2-(3H-[1,2,3]triazolo[4,5-b]pyridin-3-yl)-1,1,3,3-tetramethylisouronium hexafluorophosphate(V) (129 mg, 0.340 mmol). The reaction was allowed to stir for 1 hr then concentrated and was purified on silica gel (Biotage, EtOAc/hexanes gradient, fraction collection at λ=254 nm) to give the expected product 5-(3-(tert-butylcarbamoyl)phenyl)-6-chloro-2-(4-chlorophenyl)-N-methylfuro[2,3-b]pyridine-3-carboxamide (61 mg, 0.123 mmol, 54.2% yield) consistent by LCMS and NMR. LC-MS retention time: 3.17 min; m/z (MH+): 496. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. 1H NMR (400 MHz, CHLOROFORM-d) δ 8.19 (s, 1H), 7.93-7.86 (m, 2H), 7.81-7.76 (m, 2H), 7.63-7.57 (m, 1H), 7.56-7.49 (m, 3H), 6.02 (br. s., 1H), 5.97-5.89 (m, 1H), 3.01 (d, J=5.0 Hz, 3H), 1.50 (s, 9H)

Step 7: Preparation of Compound 4002

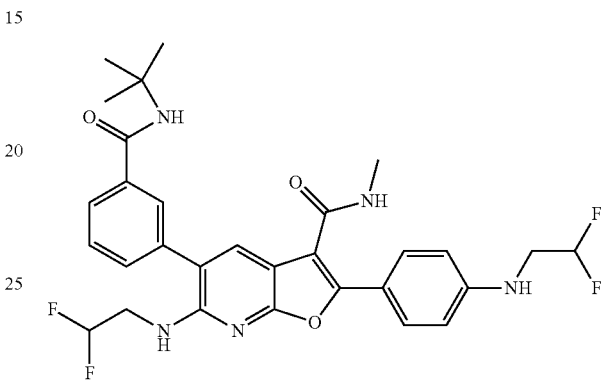

Sodium 2-methylbutan-2-olate (4.4 mg, 0.040 mmol), 5-(3-(tert-butylcarbamoyl)phenyl)-6-chloro-2-(4-chlorophenyl)-N-methylfuro[2,3-b]pyridine-3-carboxamide (10 mg, 0.020 mmol), 2,2-difluoroethanamine (3.3 mg, 0.040 mmol), Chloro[2-(dicyclohexylphosphino)-3,6-dimethoxy-2',4',6'-triisopropyl-1,1'-biphenyl][2-(2-aminoethyl)phenyl]palladium(II) (3.2 mg, 4.0 μmol) were combined, degassed, and taken up in dioxane (0.70 ml) at rt and then was heated to 80° C. for 5 minutes. The reaction was diluted with EtOAc and washed with aq. 1M HCl, and sat aq. NaCl. The organic phase was concentrated and the crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 50-90% B over 20 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. (rt: 2.95 min, M+H=586) Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. (rt: 3.94 min, M+H=586) Proton NMR was acquired in deuterated DMSO. 1H NMR (500 MHz, DMSO-d6) δ 8.21-8.13 (m, 1H), 7.87-7.79 (m, 3H), 7.68 (d, J=8.9 Hz, 2H), 7.60-7.51 (m, 3H), 6.77 (d, J=8.9 Hz, 2H), 6.50-6.43 (m, 1H), 6.36-5.99 (m, 3H), 3.82-3.69 (m, 2H), 3.63-3.51 (m, 2H), 2.77 (d, J=4.6 Hz, 3H), 1.39 (s, 9H)

Preparation of Compound 6002

Step 1: Preparation of 5-bromo-6-chloro-3-(p-tolylethynyl)pyridin-2-yl acetate

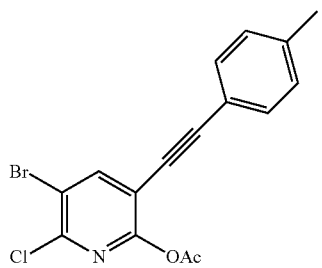 [SMILES: CC(=O)Oc1nc(Cl)c(Br)cc1C#Cc1ccc(C)cc1]

5-bromo-6-chloro-3-iodopyridin-2-yl acetate (1.0 g, 2.7 mmol) was dissolved in THF (10 mL) and cooled to 0° C. TEA (0.5 mL), copper(I)iodide (35 mg, 0.19 mmol), and bistriphenyl phosphine palladium di chloride (19 mg, 0.027 mmol) were added to the reaction mixture. The mixture was degassed and charged with N2-3×. Next, 1-ethynyl-4-methylbenzene (370 mg, 3.19 mmol) was added dropwise over the course of 2 h at 0° C. The reaction mixture was then allowed to slowly warm to rt. over the course of 18 h. LCMS and TLC show the reaction to be complete. The reaction mixture was conc. to dryness and the solids adsorbed onto SiO2 and flashed (Biotage SiO2) eluting with a 0-10% MeOH in DCM gradient over 12 CV to give 5-bromo-6-chloro-3-(p-tolylethynyl)pyridin-2-yl acetate (680 mg, 1.865 mmol, 70.2% yield) consistent by LCMS. LC-MS retention time: 3.78 min; m/z (MH+): 366. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: Preparation of 5-bromo-6-chloro-N-methyl-2-(p-tolyl)furo[2,3-b]pyridine-3-carboxamide

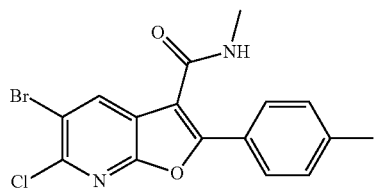 [SMILES: CNC(=O)c1c(-c2ccc(C)cc2)oc2nc(Cl)c(Br)cc12]

Sodium acetate (450 mg, 5.49 mmol), K$_2$CO$_3$ (758 mg, 5.49 mmol), copper(II) chloride dihydrate (1403 mg, 8.23 mmol), palladium(II) chloride (81 mg, 0.46 mmol), 5-bromo-6-chloro-3-(p-tolylethynyl)pyridin-2-yl acetate (1000 mg, 2.74 mmol)(in ~50 mL of THF) were combined in MeOH (27 ml) at rt in a Parr Bomb. The vessel was charged with 300 PSI of CO (minimalizing the time the reaction is devoid of CO) and allowed to stir at rt over the weekend. The reaction was concentrated and filtered through a pad of celite washing with THF. The crude methyl ester was taken up in 20 mL of THF and 20 mL of MeOH. 14 mL of 1M aq NaOH was added to the slurry and the reaction was allowed to stir at 60° C. for 1 hr. The mixture was then diluted with EtOAc and washed with aq 1M HCl, and sat aq NaCl. The organic phase was dried over Na2SO4, filtered and concentrated to give crude acid product which was then diluted with 15 mL of DMF and treated with N-ethyl-N-isopropylpropan-2-amine (2127 mg, 16.46 mmol), methanamine hydrochloride (926 mg, 13.7 mmol), and 2-(3H-[1,2,3]triazolo[4,5-b]pyridin-3-yl)-1,1,3,3-tetramethylisouronium hexafluorophosphate(V) (1147 mg, 3.02 mmol). The reaction was allowed to stir for 1 hr. The mixture was concentrated to dryness azeotroping with toluene to give crude methyl amide product. The residue was diluted with DCM and celite was added. The slurry was loaded onto a silica column and was purified on silica gel (Biotage, EtOAc/hexanes gradient, fraction collection at λ=254 nm) to give crude product which was triturated with MeOH to give white powder which was gave 400 mg of a mixture of products which was repurified on silica gel (Biotage, EtOAc/hexanes gradient followed by a 10% MeOH/DCM flushed, fraction collection at =254 nm) to give 5-bromo-6-chloro-N-methyl-2-(p-tolyl)furo[2,3-b]pyridine-3-carboxamide consistent (275 mg, 26% yield) by LCMS and NMR. LC-MS retention time: 2.14 min; m/z (MH+): 382. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 10% methanol/90% H2O/0.1% trifluoroacetic acid and solvent B was 10% H2O/90% methanol/0.1% trifluoroacetic acid. MS data was determined using a Micromass Platform for LC in electrospray mode. 1H NMR (400 MHz, METHANOL-d4) δ 8.40 (s, 1H), 7.81 (d, J=8.3 Hz, 2H), 7.36 (d, J=8.0 Hz, 2H), 2.94 (s, 3H), 2.43 (s, 3H)

Step 3: Preparation of 5-(3-(tert-butylcarbamoyl)phenyl)-6-chloro-N-methyl-2-(p-tolyl)furo[2,3-b]pyridine-3-carboxamide

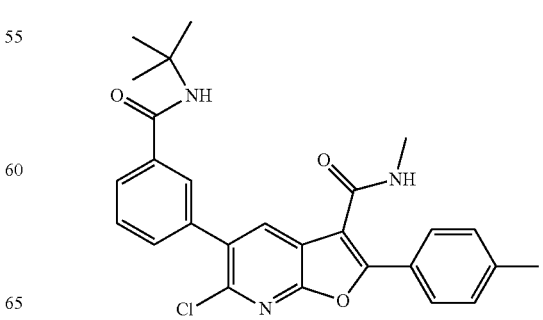

A mixture of 3-(4,4,5,5-tetramethyl-1,3,2-dioxaborolan-2-yl)benzoic acid (65 mg, 0.26 mmol), Pd(Ph₃P)₄ (30 mg, 0.026 mmol) and cesium carbonate (129 mg, 0.395 mmol) was degassed and diluted Water (0.5 ml)/DMF (5 ml). The mixture was degassed and heated to 70° C. under N2. The reaction was allowed to stir at 70° C. overnight. LCMS showed a peak with M+H of 421. The mixture was diluted with EtOAc and washed with aq 1M HCl, and sat aq NaCl. The organic phase was dried over Na2SO4, filtered and concentrated azeotroping with toluene. The crude solid was diluted with 5 mL of DMF and treated with 2-methylpropan-2-amine (38 mg, 0.53 mmol), N-ethyl-N-isopropylpropan-2-amine (102 mg, 0.790 mmol) followed by 2-(3H-[1,2,3]triazolo[4,5-b]pyridin-3-yl)-1,1,3,3-tetramethylisouronium hexafluorophosphate(V) (150 mg, 0.395 mmol). LCMS after 1 hr of stirring showed peak with M+H of 476. The reaction was concentrated and purified on silica gel (Biotage, EtOAc/hexanes gradient, fraction collection at λ=254 nm) to give the expected product 5-(3-(tert-butylcarbamoyl)phenyl)-6-chloro-N-methyl-2-(p-tolyl)furo[2,3-b]pyridine-3-carboxamide (61 mg, 0.13 mmol, 49% yield) consistent by LCMS. LC-MS retention time: 2.31 min; m/z (MH+): 476. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 10% methanol/90% H2O/0.1% trifluoroacetic acid and solvent B was 10% H2O/90% methanol/0.1% trifluoroacetic acid. MS data was determined using a Micromass Platform for LC in electrospray mode.

Step 4: Preparation of Compound 6002

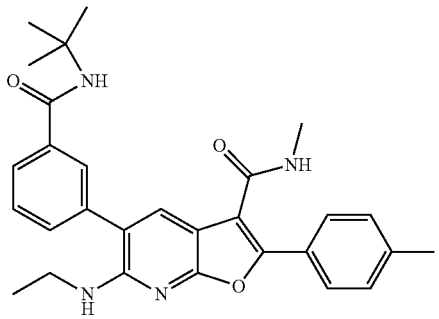 [SMILES: CCNc1nc2oc(-c3ccc(C)cc3)c(C(=O)NC)c2cc1-c1cccc(C(=O)NC(C)(C)C)c1]

Sodium 2-methylbutan-2-olate (69 mg, 0.63 mmol), 5-(3-(tert-butylcarbamoyl)phenyl)-6-chloro-N-methyl-2-(p-tolyl)furo[2,3-b]pyridine-3-carboxamide (30 mg, 0.063 mmol), ethanamine hydrochloride (103 mg, 1.26 mmol), Chloro[2-(dicyclohexylphosphino)-3,6-dimethoxy-2',4',6'-triisopropyl-1,1'-biphenyl][2-(2-aminoethyl)phenyl]palladium(II) (5.0 mg, 6.3 μmol) were combined in dioxane (1.3 ml) at 100° C. under an inert atmosphere (N2). LCMS within 1 hr showed major peak with M+H of 485. The reaction was purified by preparative reverse phase HPLC on a C18 column using a suitably buffered H2O/CH3CN gradient, and pure fractions were concentrated to give the expected product 5-(3-(tert-butylcarbamoyl)phenyl)-6-(ethylamino)-N-methyl-2-(p-tolyl)furo[2,3-b]pyridine-3-carboxamide (12 mg, 0.024 mmol, 37% yield) consistent by LCMS and NMR. LC-MS retention time: 2.75 min; m/z (MH+): 485. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. 1H NMR (400 MHz, CHLOROFORM-d) δ 7.83-7.68 (m, 5H), 7.58-7.49 (m, 2H), 7.29 (d, J=8.0 Hz, 2H), 6.15 (s, 1H), 6.05-5.94 (m, 1H), 3.49 (q, J=7.1 Hz, 2H), 2.94 (d, J=4.8 Hz, 3H), 2.43 (s, 3H), 1.50 (s, 9H), 1.19 (t, J=7.2 Hz, 3H)

Preparation of Compound 6003

Step 1: Preparation of 6-chloro-N-methyl-2-(p-tolyl)-5-(3-((1-(trifluoromethyl)cyclopropyl)carbamoyl)phenyl)furo[2,3-b]pyridine-3-carboxamide

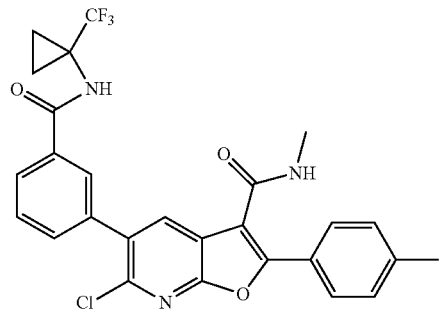 [SMILES: CNC(=O)c1c(-c2ccc(C)cc2)oc2nc(Cl)c(-c3cccc(C(=O)NC4(C(F)(F)F)CC4)c3)cc12]

A mixture of 5-bromo-6-chloro-N-methyl-2-(p-tolyl)furo[2,3-b]pyridine-3-carboxamide (48 mg, 0.13 mmol), 3-(4,4,5,5-tetramethyl-1,3,2-dioxaborolan-2-yl)benzoic acid (31 mg, 0.13 mmol), Pd(Ph3P)4 (15 mg, 0.013 mmol) and cesium carbonate (62 mg, 0.19 mmol) was degassed and diluted Water (0.23 ml)/DMF (2.3 ml). The mixture was degassed and heated to 70° C. under N2. The reaction was allowed to stir at 70° C. overnight. The mixture was diluted with EtOAc and washed with aq 1M HCl, and sat aq NaCl. The organic phase was dried over Na2SO4, filtered and concentrated. The crude solid was diluted with 5 mL of DMF and treated with 1-(trifluoromethyl)cyclopropanamine (32 mg, 0.25 mmol), N-ethyl-N-isopropylpropan-2-amine (49 mg, 0.38 mmol) followed by 2-(3H-[1,2,3]triazolo[4,5-b]pyridin-3-yl)-1,1,3,3-tetramethylisouronium hexafluorophosphate(V) (72 mg, 0.19 mmol). The reaction was allowed to stir until LCMS showed the reaction was complete. The reaction then was concentrated and triturated with DCM to give 6-chloro-N-methyl-2-(p-tolyl)-5-(3-((1-(trifluoromethyl)cyclopropyl)carbamoyl)phenyl)furo[2,3-b]pyridine-3-carboxamide (78 mg) consistent by LCMS. LC-MS retention time: 1.74 min; m/z (MH+): 528. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: Preparation of Compound 6003

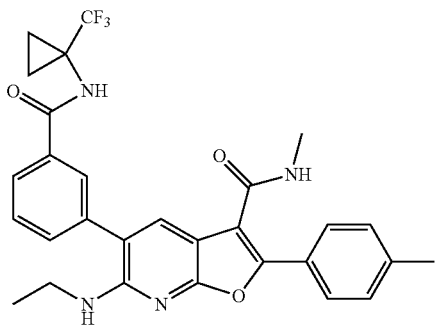 [SMILES: CCNc1nc2oc(-c3ccc(C)cc3)c(C(=O)NC)c2cc1-c1cccc(C(=O)NC2(C(F)(F)F)CC2)c1]

sodium 2-methylbutan-2-olate (81 mg, 0.74 mmol) 6-chloro-N-methyl-2-(p-tolyl)-5-(3-((1-(trifluoromethyl)cyclopropyl)carbamoyl)phenyl)furo[2,3-b]pyridine-3-carboxamide (39 mg, 0.074 mmol), ethanamine hydrochloride (120 mg, 1.48 mmol), Chloro[2-(dicyclohexylphosphino)-3,6-dimethoxy-2',4',6'-triisopropyl-1,1'-biphenyl][2-(2-aminoethyl)phenyl]palladium(II) (3.0 mg, 3.7 μmol), in dioxane (0.8 ml) at 100° C. LCMS after 1 hr showed peak with M+H of 537. The reaction was purified by preparative reverse phase HPLC on a C18 column using a suitably buffered H2O/CH3CN gradient, and concentrated. The reaction was repeated with similar results and the isolated material was combined to give the expected product 6-(ethylamino)-N-methyl-2-(p-tolyl)-5-(3-((1-(trifluoromethyl)cyclopropyl)carbamoyl)phenyl)furo[2,3-b]pyridine-3-carboxamide (4 mg, 7.08 μmol, 10% yield) consistent by LCMS and NMR. LC-MS retention time: 2.25 min; m/z (MH+): 537. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 10% methanol/90% H2O/0.1% trifluoroacetic acid and solvent B was 10% H2O/90% methanol/0.1% trifluoroacetic acid. 1H NMR (400 MHz, CHLOROFORM-d) δ 7.86-7.80 (m, 2H), 7.78-7.71 (m, 3H), 7.64-7.53 (m, 2H), 7.32-7.29 (m, 2H), 6.76 (s, 1H), 5.94-5.85 (m, 1H), 3.50 (q, J=7.2 Hz, 2H), 2.94 (d, J=5.0 Hz, 3H), 2.43 (s, 3H), 1.49-1.43 (m, 2H), 1.32-1.26 (m, 2H), 1.20 (t, J=7.2 Hz, 3H).

Biological Methods

The compound demonstrated activity against HCV NS5B as determined in the following HCV RdRp assays.

HCV NS5B RdRp Cloning, Expression, and Purification.

The cDNA encoding NS5B proteins of HCV genotype 1b (Con1), a genotype 1b variant with amino acid 316 mutated from cysteine to asparagine, and genotype 2a (JFH-1), were cloned into the pET21a expression vector. Each untagged protein was expressed with an 18 amino acid C-terminal truncation to enhance the solubility. The E. coli competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM MgCl$_2$, 15 ug/mL deoxyribonuclease I, and Complete™ protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 μm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, MgCl$_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCV NS5B RdRp Enzyme Assay.

An on-bead solid phase homogeneous assay was used in a 384-well format to assess NS5B inhibitors (Wang Y-K, Rigat K, Roberts S, and Gao M (2006) Anal Biochem, 359: 106-111). The biotinylated oligo dT$_{12}$ primer was captured on streptavidin-coupled imaging beads (GE, RPNQ0261) by mixing primer and beads in 1× buffer and incubating at room temperature for three hours. Unbound primer was removed after centrifugation. The primer-bound beads were resuspended in 3× reaction mix (20 mM Hepes buffer, pH 7.5, dT primer coupled beads, poly A template, $^3$H-UTP, and RNAse inhibitor (Promega N2515)). Compounds were serially diluted 1:3 in DMSO and aliquoted into assay plates. Equal volumes (5 μL) of water, 3× reaction mix, and enzyme in 3× assay buffer (60 mM Hepes buffer, pH 7.5, 7.5 mM MgCl$_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 μM $^3$H-UTP (0.3 μCi), 1.6 U/μL RNAse inhibitor, 7 nM NS5B enzyme, 0.01 mg/mL BSA, 1 mM DTT, and 0.33 μg/μL beads, 20 mM Hepes buffer, pH 7.5, 2.5 mM MgCl$_2$, 2.5 mM KCl, and 0.1% DMSO.

Reactions were allowed to proceed for 24 hours at 30° C. and terminated by the addition of 50 mM EDTA (5 μL). After incubating for at least 15 minutes, plates were read on an Amersham LEADseeker multimodality imaging system.

IC$_{50}$ values for compounds were determined using ten different [I]. IC$_{50}$ values were calculated from the inhibition using the four-parameter logistic formula y=A+((B−A)/(1+((C/x)^D))), where A and B denote minimal and maximal % inhibition, respectively, C is the IC$_{50}$, D is hill slope and x represents compound concentration.

Cell Lines.

The cell lines used to evaluate compounds consist of a human hepatocyte derived cell line (Huh-7) that constitutively expresses a genotype 1b (Con-1) HCV replicon or a genotype 1b (Con-1) HCV replicon with an asparagine replacing the cysteine at amino acid 316, or a genotype 2a (JFH-1) replicon, containing a *Renilla* luciferase reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay.

To evaluate compound efficacy, titrated compounds were transferred to sterile 384-well tissue culture treated plates, and the plates were seeded with HCV replicon cells (50 μL at a density of $2.4 \times 10^3$ cells/well) in DMEM containing 4% FBS (final DMSO concentration at 0.5%). After 3 days incubation at 37° C., cells were analyzed for *Renilla* Luciferase activity using the EnduRen substrate (Promega cat #E6485) according to the manufacturer's directions. Briefly, the EnduRen substrate was diluted in DMEM and then added to the plates to a final concentration of 7.5 μM. The plates were incubated for at least 1 h at 37° C. then read on a Viewlux Imager (PerkinElmer) using a luminescence program. The 50% effective concentration ($EC_{50}$) was calculated using the four-parameter logistic formula noted above.

To assess cytotoxicity of the compounds, Cell Titer-Blue (Promega) was added to the EnduRen-containing plates and incubated for at least 4 hrs at 37° C. The fluorescence signal from each well was read using a Viewlux Imager. All $CC_{50}$ values were calculated using the four-parameter logistic formula.

Compound $EC_{50}$ data is expressed as A: <100 nM; B=100-1000 nM; C>1000 nM). Representative data for compounds are reported in Table 2.

TABLE 2

| Cmpd # | Structure | $EC_{50}$ (uM) 1b |
|---|---|---|
| 1001 | 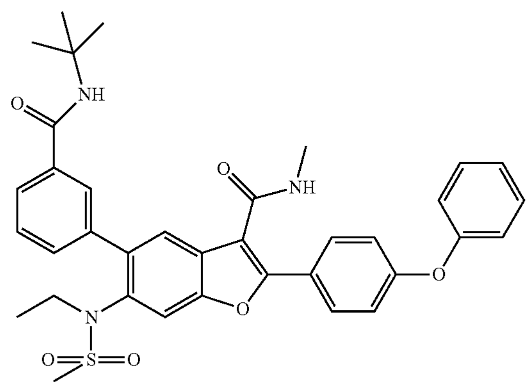 [SMILES: CCN(c1cc2oc(-c3ccc(Oc4ccccc4)cc3)c(C(=O)NC)c2cc1-c1cccc(C(=O)NC(C)(C)C)c1)S(C)(=O)=O] | A |
| 1002 | 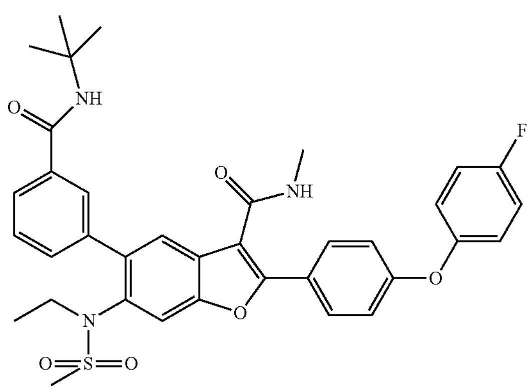 | A |
| 1003 | 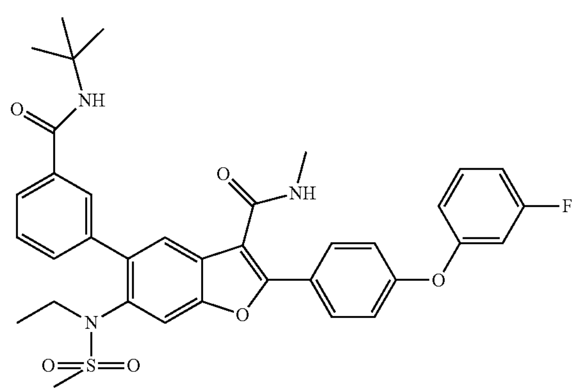 [SMILES: CCN(c1cc2oc(-c3ccc(Oc4cccc(F)c4)cc3)c(C(=O)NC)c2cc1-c1cccc(C(=O)NC(C)(C)C)c1)S(C)(=O)=O] | 0.0023 A |

TABLE 2-continued
| Cmpd # | Structure | EC$_{50}$ (uM) 1b |
|---|---|---|
| 1004 | 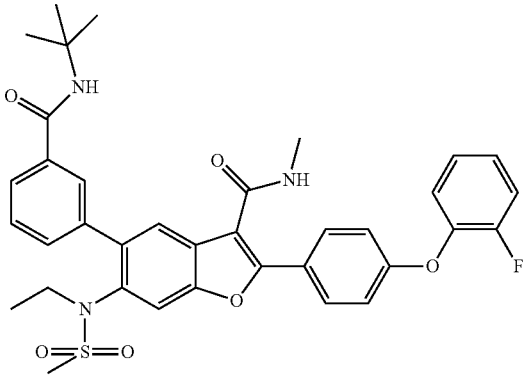 [SMILES: CCN(c1cc2oc(-c3ccc(Oc4ccccc4F)cc3)c(C(=O)NC)c2cc1-c1cccc(C(=O)NC(C)(C)C)c1)S(C)(=O)=O] | A |
| 1005 | 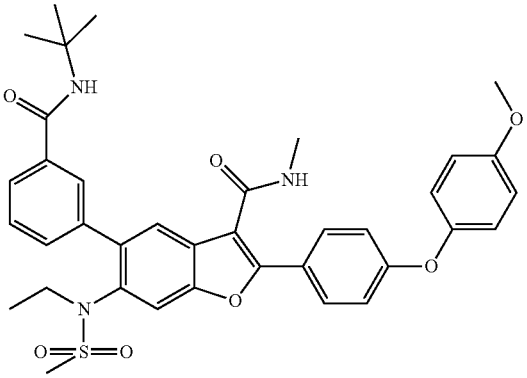 [SMILES: CCN(c1cc2oc(-c3ccc(Oc4ccc(OC)cc4)cc3)c(C(=O)NC)c2cc1-c1cccc(C(=O)NC(C)(C)C)c1)S(C)(=O)=O] | 0.12 B |
| 1006 | 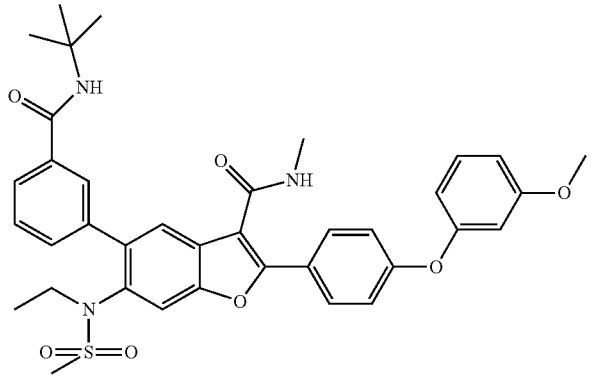 [SMILES: CCN(c1cc2oc(-c3ccc(Oc4cccc(OC)c4)cc3)c(C(=O)NC)c2cc1-c1cccc(C(=O)NC(C)(C)C)c1)S(C)(=O)=O] | A |
| 1007 | 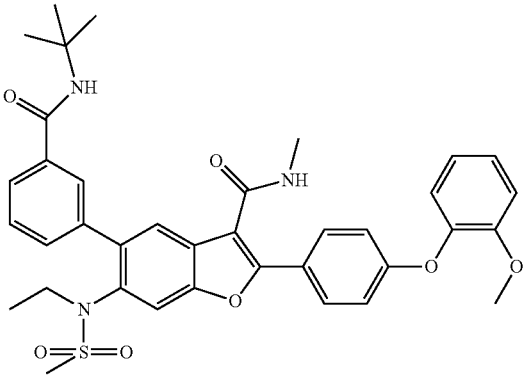 | 0.024 A |

TABLE 2-continued
| Cmpd # | Structure | EC$_{50}$ (uM) 1b |
|---|---|---|
| 1008 | 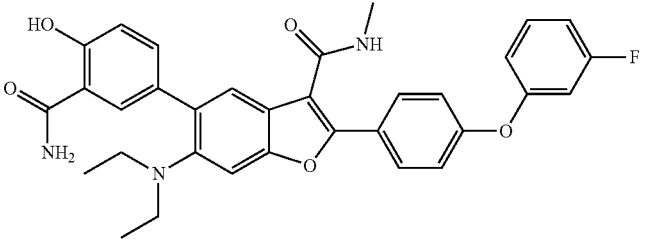 [SMILES: CCN(CC)c1cc2oc(-c3ccc(Oc4cccc(F)c4)cc3)c(C(=O)NC)c2cc1-c1ccc(O)c(C(N)=O)c1] | 0.013 A |
| 1010 | 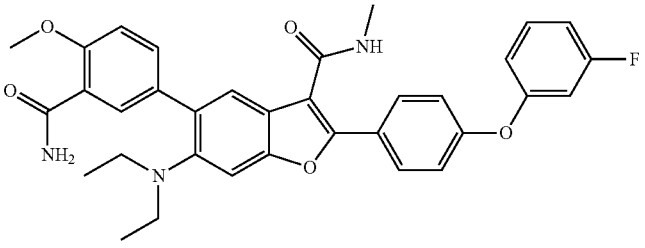 [SMILES: CCN(CC)c1cc2oc(-c3ccc(Oc4cccc(F)c4)cc3)c(C(=O)NC)c2cc1-c1ccc(OC)c(C(N)=O)c1] | B |
| 1012 | 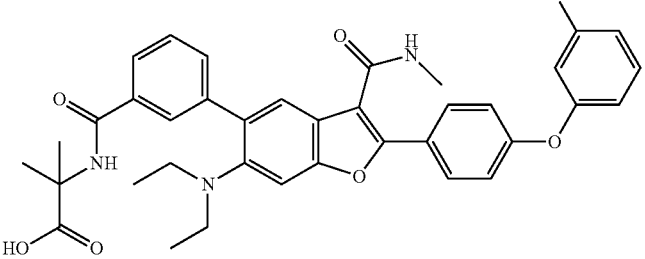 | 1.47 C |
| 1013 | 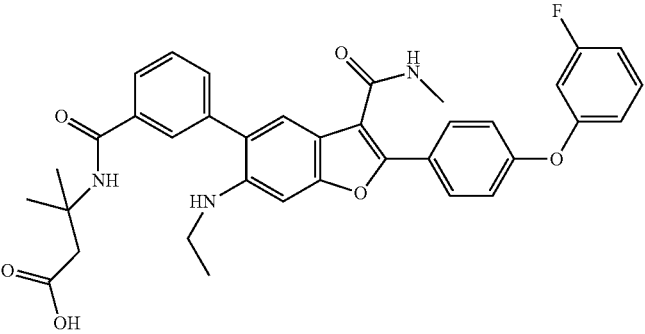 [SMILES: CCNc1cc2oc(-c3ccc(Oc4cccc(F)c4)cc3)c(C(=O)NC)c2cc1-c1cccc(C(=O)NC(C)(C)CC(=O)O)c1] | B |
| 1014 | 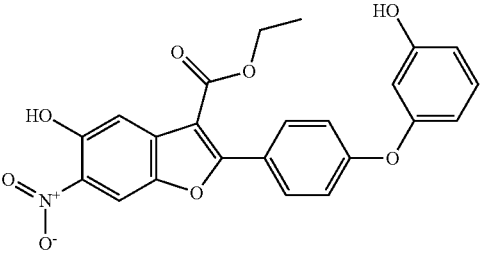 [SMILES: CCOC(=O)c1c(-c2ccc(Oc3cccc(O)c3)cc2)oc2cc([N+](=O)[O-])c(O)cc12] | 9.94 C |

TABLE 2-continued

| Cmpd # | Structure | EC$_{50}$ (uM) 1b |
|---|---|---|
| 1015 | 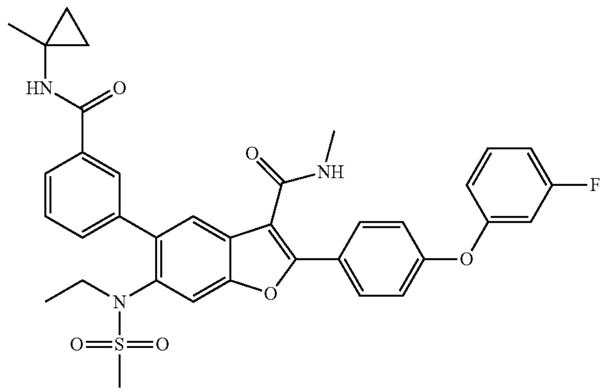 [SMILES: CCN(c1cc2oc(-c3ccc(Oc4cccc(F)c4)cc3)c(C(=O)NC)c2cc1-c1cccc(C(=O)NC2(C)CC2)c1)S(C)(=O)=O] | C |
| 1016 | 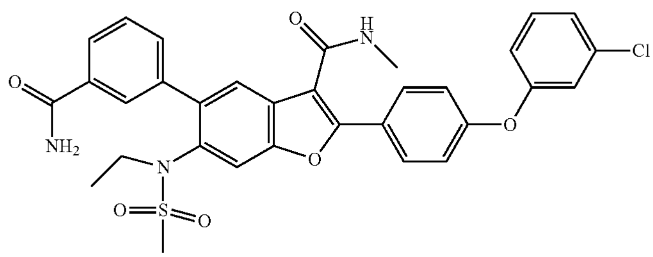 [SMILES: CCN(c1cc2oc(-c3ccc(Oc4cccc(Cl)c4)cc3)c(C(=O)NC)c2cc1-c1cccc(C(N)=O)c1)S(C)(=O)=O] | A |
| 1017 | 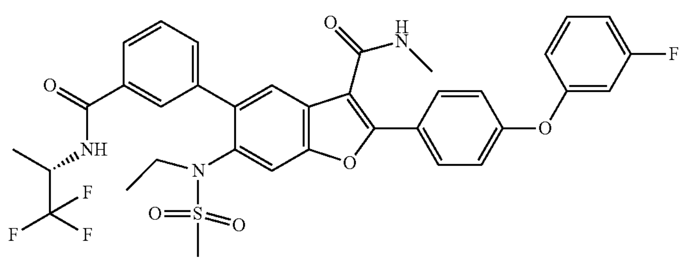 [SMILES: CCN(c1cc2oc(-c3ccc(Oc4cccc(F)c4)cc3)c(C(=O)NC)c2cc1-c1cccc(C(=O)N[C@@H](C)C(F)(F)F)c1)S(C)(=O)=O] | 0.0062 A |
| 1018 | 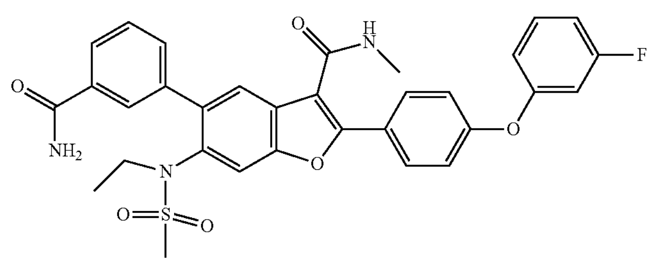 [SMILES: CCN(c1cc2oc(-c3ccc(Oc4cccc(F)c4)cc3)c(C(=O)NC)c2cc1-c1cccc(C(N)=O)c1)S(C)(=O)=O] | A |
| 1019 | 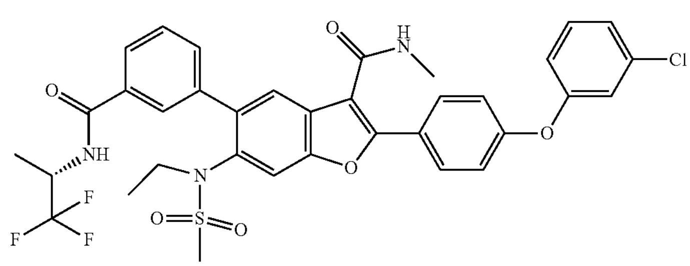 [SMILES: CCN(c1cc2oc(-c3ccc(Oc4cccc(Cl)c4)cc3)c(C(=O)NC)c2cc1-c1cccc(C(=O)N[C@@H](C)C(F)(F)F)c1)S(C)(=O)=O] | A |

TABLE 2-continued

| Cmpd # | Structure | EC$_{50}$ (uM) 1b |
|---|---|---|
| 1020 | 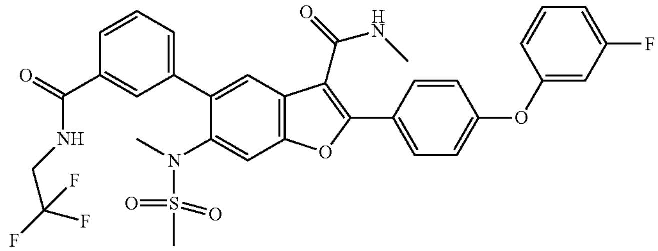 [SMILES: CNC(=O)c1c(-c2ccc(Oc3cccc(F)c3)cc2)oc2cc(N(C)S(C)(=O)=O)c(-c3cccc(C(=O)NCC(F)(F)F)c3)cc12] | A |
| 1021 | 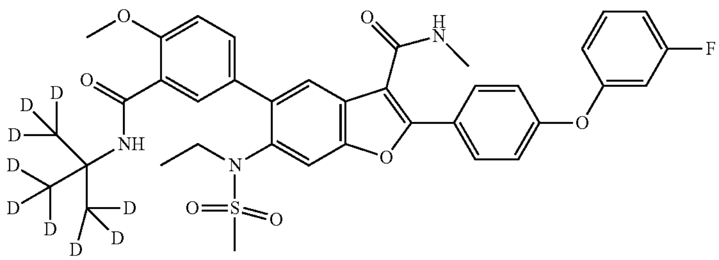 [SMILES: [2H]C([2H])([2H])C(NC(=O)c1cc(-c2cc3c(C(=O)NC)c(-c4ccc(Oc5cccc(F)c5)cc4)oc3cc2N(CC)S(C)(=O)=O)ccc1OC)(C([2H])([2H])[2H])C([2H])([2H])[2H]] | A |
| 1022 | 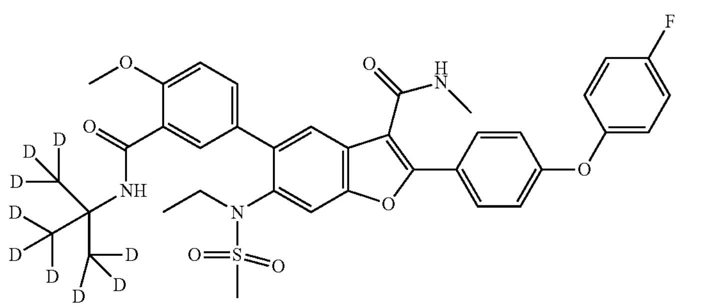 [SMILES: [2H]C([2H])([2H])C(NC(=O)c1cc(-c2cc3c(C(=O)NC)c(-c4ccc(Oc5ccc(F)cc5)cc4)oc3cc2N(CC)S(C)(=O)=O)ccc1OC)(C([2H])([2H])[2H])C([2H])([2H])[2H]] | A |
| 1023 | 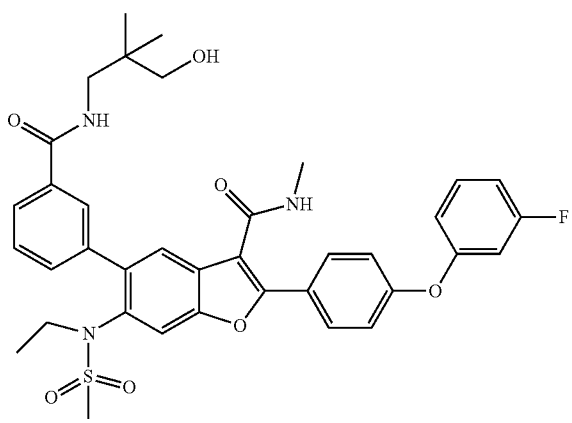 [SMILES: CCN(c1cc2oc(-c3ccc(Oc4cccc(F)c4)cc3)c(C(=O)NC)c2cc1-c1cccc(C(=O)NCC(C)(C)CO)c1)S(C)(=O)=O] | 0.0028 A |
| 1026 | 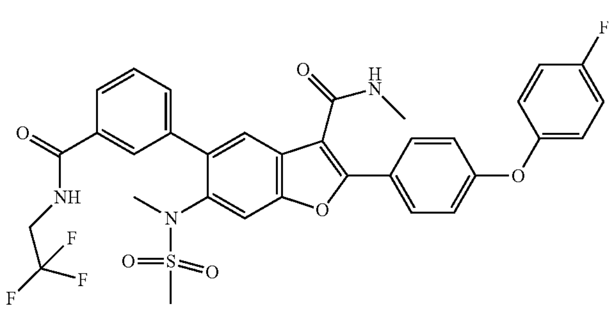 [SMILES: CNC(=O)c1c(-c2ccc(Oc3ccc(F)cc3)cc2)oc2cc(N(C)S(C)(=O)=O)c(-c3cccc(C(=O)NCC(F)(F)F)c3)cc12] | A |

TABLE 2-continued

| Cmpd # | Structure | EC$_{50}$ (uM) 1b |
|---|---|---|
| 2001 | 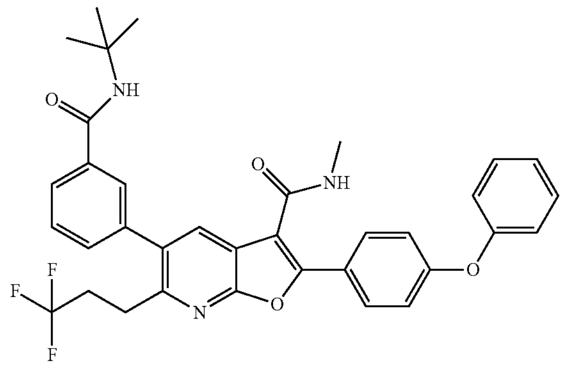 | A |
| 2002 | 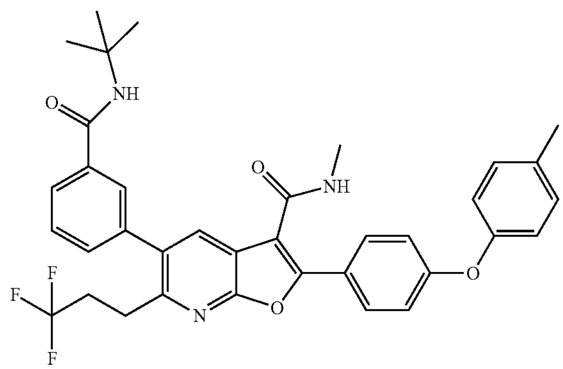 [SMILES: CNC(=O)c1c(-c2ccc(Oc3ccc(C)cc3)cc2)oc2nc(CCC(F)(F)F)c(-c3cccc(C(=O)NC(C)(C)C)c3)cc12] | A |
| 2003 | 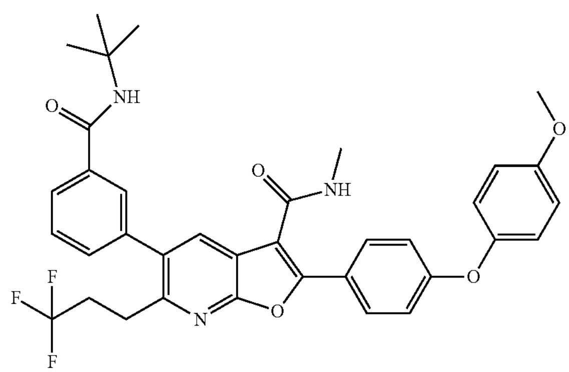 [SMILES: CNC(=O)c1c(-c2ccc(Oc3ccc(OC)cc3)cc2)oc2nc(CCC(F)(F)F)c(-c3cccc(C(=O)NC(C)(C)C)c3)cc12] | B |
| 2004 | 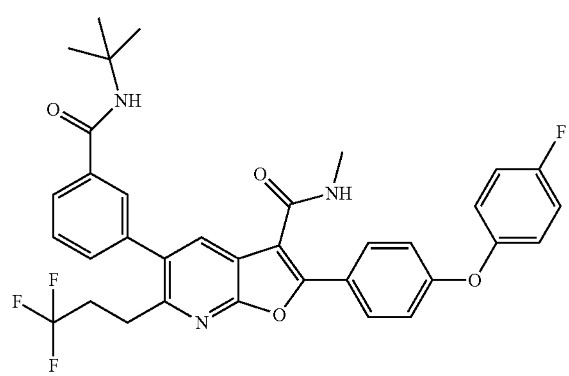 [SMILES: CNC(=O)c1c(-c2ccc(Oc3ccc(F)cc3)cc2)oc2nc(CCC(F)(F)F)c(-c3cccc(C(=O)NC(C)(C)C)c3)cc12] | A |

TABLE 2-continued

| Cmpd # | Structure | EC$_{50}$ (uM) 1b |
|---|---|---|
| 2005 | 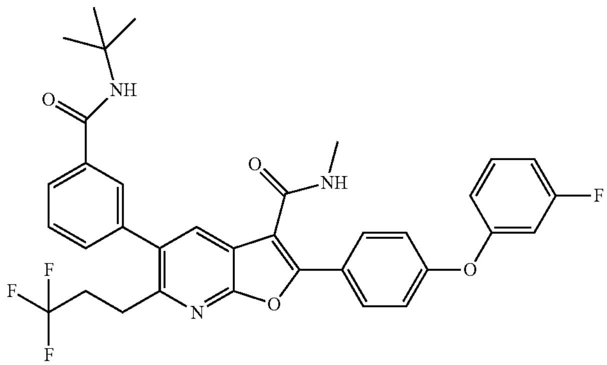 [SMILES: CNC(=O)c1c(-c2ccc(Oc3cccc(F)c3)cc2)oc2nc(CCC(F)(F)F)c(-c3cccc(C(=O)NC(C)(C)C)c3)cc12] | A |
| 2006 | 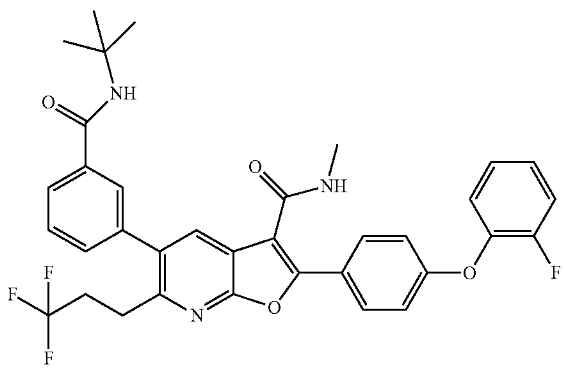 [SMILES: CNC(=O)c1c(-c2ccc(Oc3ccccc3F)cc2)oc2nc(CCC(F)(F)F)c(-c3cccc(C(=O)NC(C)(C)C)c3)cc12] | A |
| 2007 | 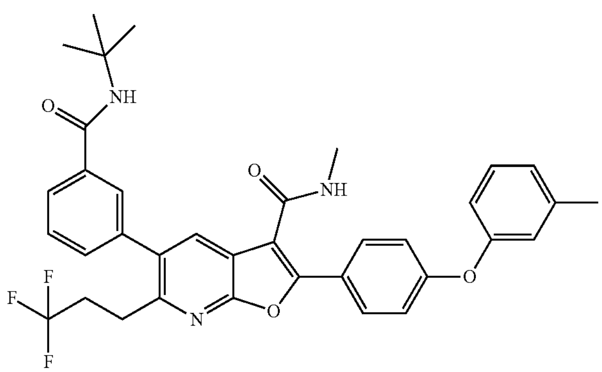 [SMILES: CNC(=O)c1c(-c2ccc(Oc3cccc(C)c3)cc2)oc2nc(CCC(F)(F)F)c(-c3cccc(C(=O)NC(C)(C)C)c3)cc12] | A |
| 2008 | 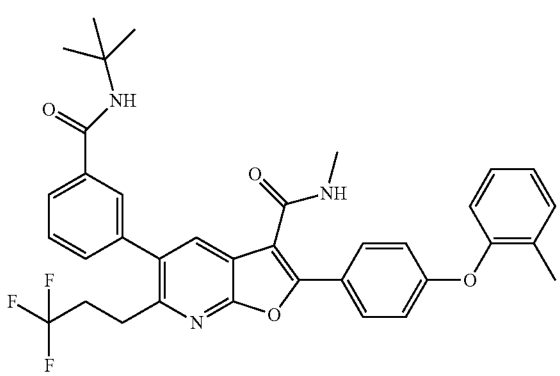 [SMILES: CNC(=O)c1c(-c2ccc(Oc3ccccc3C)cc2)oc2nc(CCC(F)(F)F)c(-c3cccc(C(=O)NC(C)(C)C)c3)cc12] | A |

TABLE 2-continued

| Cmpd # | Structure | EC$_{50}$ (uM) 1b |
|---|---|---|
| 2009 | 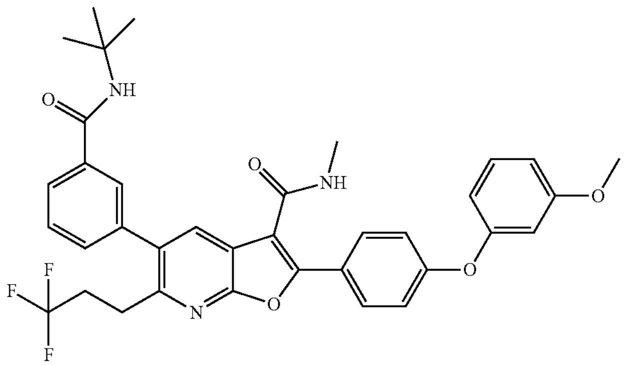 [SMILES: CNC(=O)c1c(-c2ccc(Oc3cccc(OC)c3)cc2)oc2nc(CCC(F)(F)F)c(-c3cccc(C(=O)NC(C)(C)C)c3)cc12] | A |
| 2010 | 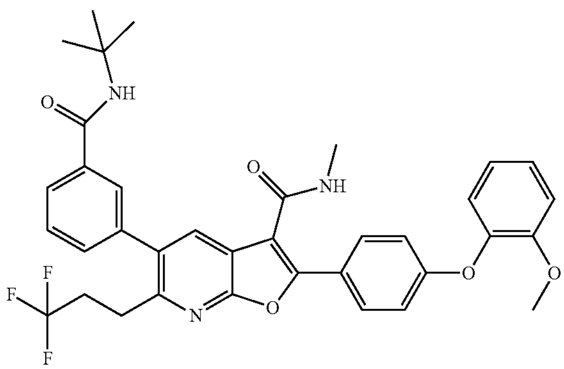 [SMILES: CNC(=O)c1c(-c2ccc(Oc3ccccc3OC)cc2)oc2nc(CCC(F)(F)F)c(-c3cccc(C(=O)NC(C)(C)C)c3)cc12] | A |
| 2011 | 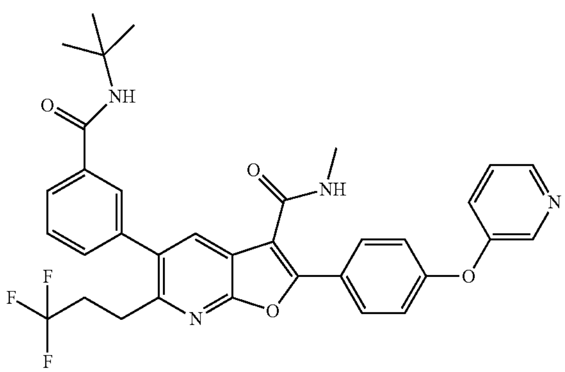 [SMILES: CNC(=O)c1c(-c2ccc(Oc3cccnc3)cc2)oc2nc(CCC(F)(F)F)c(-c3cccc(C(=O)NC(C)(C)C)c3)cc12] | A |
| 2012 | 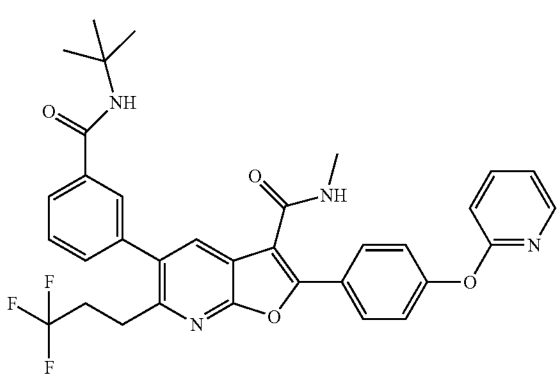 [SMILES: CNC(=O)c1c(-c2ccc(Oc3ccccn3)cc2)oc2nc(CCC(F)(F)F)c(-c3cccc(C(=O)NC(C)(C)C)c3)cc12] | C |

TABLE 2-continued

| Cmpd # | Structure | EC$_{50}$ (uM) 1b |
|---|---|---|
| 2013 | 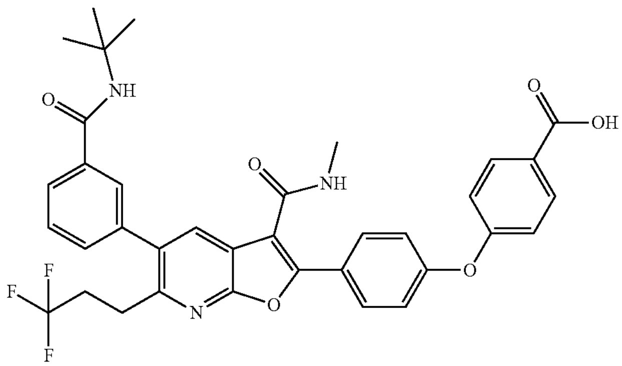 [SMILES: CNC(=O)c1c(-c2ccc(Oc3ccc(C(=O)O)cc3)cc2)oc2nc(CCC(F)(F)F)c(-c3cccc(C(=O)NC(C)(C)C)c3)cc12] | C |
| 2014 | 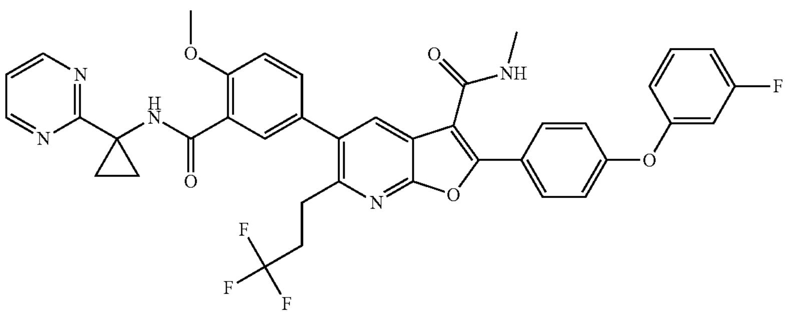 [SMILES: CNC(=O)c1c(-c2ccc(Oc3cccc(F)c3)cc2)oc2nc(CCC(F)(F)F)c(-c3ccc(OC)c(C(=O)NC4(c5ncccn5)CC4)c3)cc12] | A |
| 3001 | 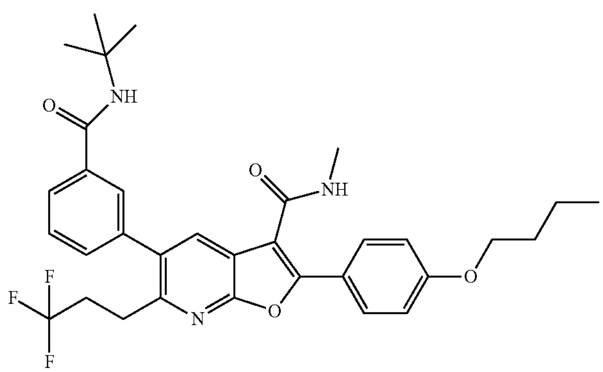 [SMILES: CCCCOc1ccc(-c2oc3nc(CCC(F)(F)F)c(-c4cccc(C(=O)NC(C)(C)C)c4)cc3c2C(=O)NC)cc1] | A |
| 3002 | 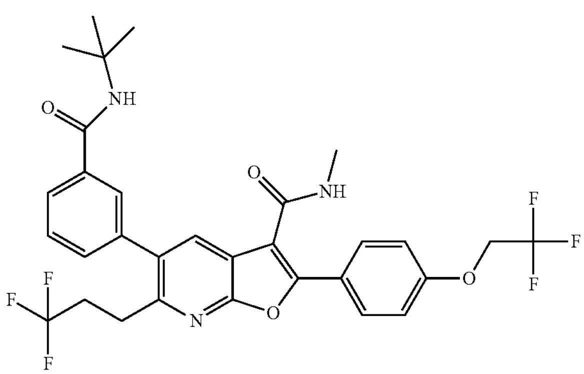 [SMILES: CNC(=O)c1c(-c2ccc(OCC(F)(F)F)cc2)oc2nc(CCC(F)(F)F)c(-c3cccc(C(=O)NC(C)(C)C)c3)cc12] | A |

TABLE 2-continued

| Cmpd # | Structure | EC$_{50}$ (uM) 1b |
|---|---|---|
| 4001 | 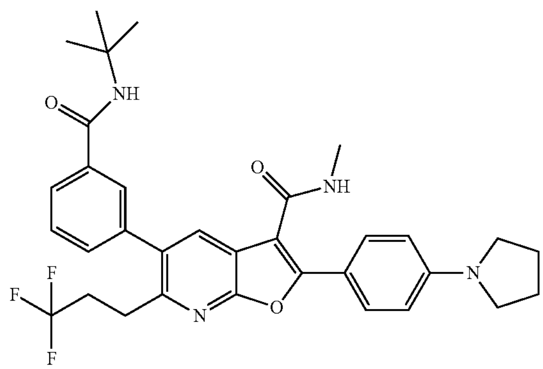 [SMILES: CNC(=O)c1c(-c2ccc(N3CCCC3)cc2)oc2nc(CCC(F)(F)F)c(-c3cccc(C(=O)NC(C)(C)C)c3)cc12] | C |
| 4002 | 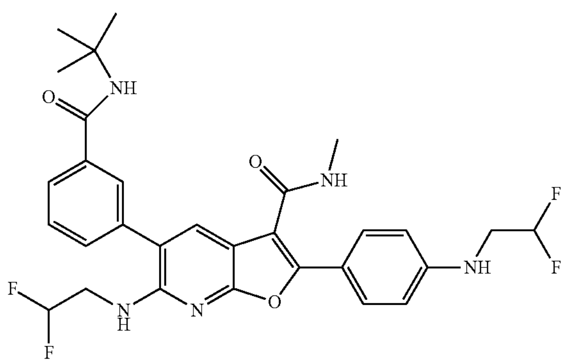 [SMILES: CNC(=O)c1c(-c2ccc(NCC(F)F)cc2)oc2nc(NCC(F)F)c(-c3cccc(C(=O)NC(C)(C)C)c3)cc12] | 0.0094 A |
| 5001 | 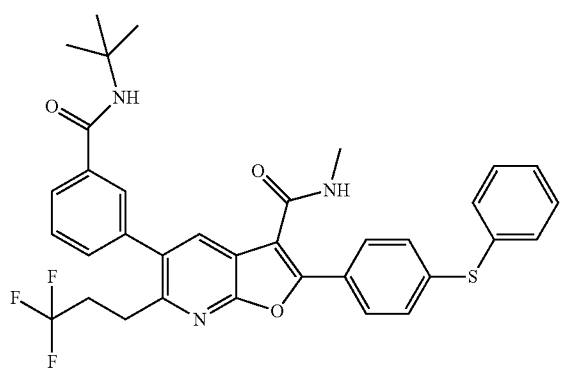 | 0.16 B |
| 6001 | 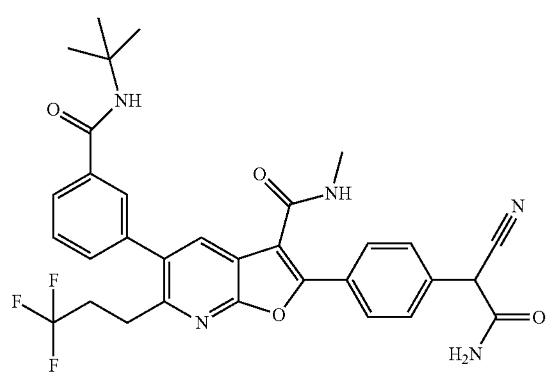 [SMILES: CNC(=O)c1c(-c2ccc(C(C#N)C(N)=O)cc2)oc2nc(CCC(F)(F)F)c(-c3cccc(C(=O)NC(C)(C)C)c3)cc12] | 0.34 B |

TABLE 2-continued

| Cmpd # | Structure | EC$_{50}$ (uM) 1b |
|---|---|---|
| 6002 | 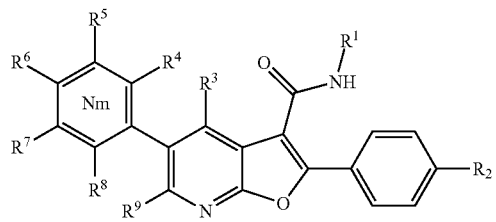 | 0.0036 A |
| 6003 | 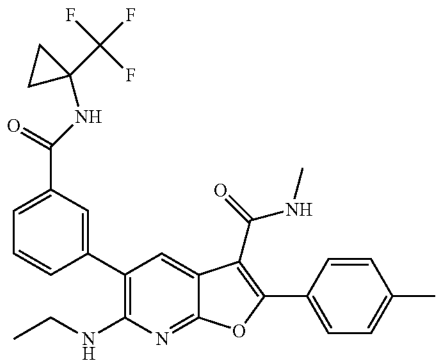 [SMILES: CCNc1nc2oc(-c3ccc(C)cc3)c(C(=O)NC)c2cc1-c1cccc(C(=O)NC2(C(F)(F)F)CC2)c1] | 0.0061 A |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I, or a pharmaceutically acceptable salt thereof:

wherein
X is N or C—R$^{10}$;
R$^1$ is methyl;
R$^2$ is OAr$^1$;
Ar$^1$ is phenyl or pyridinyl and is substituted with 0-3 substituents selected from the group of cyano, halo, alkyl, cycloalkyl, haloalkyl, hydroxy, alkoxy, and haloalkoxy;
R$^3$ is hydrogen, halo, or alkyl;
R$^4$, R$^5$, R$^6$, R$^7$, R$^8$ are each independently selected from the group of hydrogen, halo, alkyl, cycloalkyl, haloalkyl, halocycloalkyl, hydroxyalkyl, hydroxycycloalkyl, alkoxyalkyl, alkoxycycloalkyl, alkoxy, hydroxyalkyloxy, alkoxyalkyloxy, and CON(R$^{202}$)(R$^{203}$);
R$^{202}$ and R$^{203}$ are each independently selected from the group of hydrogen, alkyl, and cycloalkyl;
R$^9$ is selected from the group of haloalkyl and NR$^{301}$R$^{302}$;
R$^{301}$ is selected from the group of hydrogen, alkyl, cycloalkyl, (cycloalkyl)alkyl, benzyl, alkylcarbonyl, haloalkylcarbonyl, alkyl sulfonyl, phenyl sulfonyl, (alkoxyphenyl)sulfonyl and (haloalkoxyphenyl)sulfonyl;
R$^{302}$ is hydrogen, alkyl, hydroxyalkyl, or alkoxyalkyl; and
R$^{10}$ is hydrogen.

2. The compound of claim 1, wherein R$^5$ is CON(R$^{202}$)(R$^{203}$), or a pharmaceutically acceptable salt thereof.

3. The compound of claim 2, wherein R$^{202}$ and R$^{203}$ are each hydrogen or alkyl, or a pharmaceutically acceptable salt thereof.

4. The compound of claim 1, wherein R$^9$ is NR$^{301}$R$^{302}$, or a pharmaceutically acceptable salt thereof.

5. The compound of claim 4, wherein R$^{301}$ is hydrogen, alkyl or alkylsulfonyl, or a pharmaceutically acceptable salt thereof.

6. The compound of claim 5, wherein R$^{302}$ is alkyl, or a pharmaceutically acceptable salt thereof.

7. A composition comprising a compound of claim 1, or a pharmaceutically acceptable salt thereof, and a pharmaceutically acceptable carrier, excipient and/or diluent.

8. A method of treating hepatitis C infection comprising administering a therapeutically effective amount of a compound of claim 1 to a patient.

\* \* \* \* \*

UNITED STATES PATENT AND TRADEMARK OFFICE
CERTIFICATE OF CORRECTION

PATENT NO. : 10,214,534 B2
APPLICATION NO. : 15/317541
DATED : February 26, 2019
INVENTOR(S) : Tao Wang et al.

Page 1 of 1

It is certified that error appears in the above-identified patent and that said Letters Patent is hereby corrected as shown below:

In the Claims

In Claim 1, Column 117, Line 50-59:

Delete " 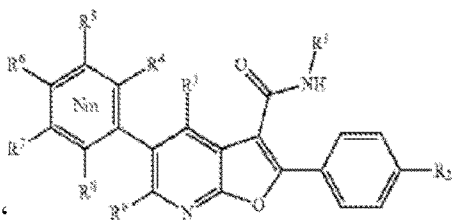 " and insert -- 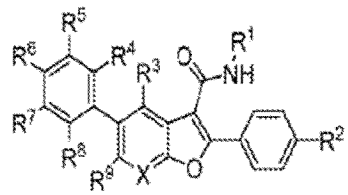 --

In Claim 1, Column 118, Line 47:
Delete "alkyl sulfonyl, phenyl sulfonyl," and insert -- alkylsulfonyl, phenylsulfonyl, --

Signed and Sealed this
Twenty-second Day of December, 2020

Andrei Iancu
*Director of the United States Patent and Trademark Office*